(12) United States Patent
Diwan et al.

(10) Patent No.: US 9,770,442 B2
(45) Date of Patent: Sep. 26, 2017

(54) SELF-ASSEMBLING AMPHIPHILIC POLYMERS AS ANTI-CANCER AGENTS

(75) Inventors: Anil Diwan, West Haven, CT (US); Ann Louise Onton, Woodbridge, CT (US); Jayant G. Tatake, Sandy Hook, CT (US)

(73) Assignee: AllExcel Inc., West Haven, CT (US)

( * ) Notice: Subject to any disclaimer, the term of this patent is extended or adjusted under 35 U.S.C. 154(b) by 818 days.

(21) Appl. No.: 12/669,245

(22) PCT Filed: Jul. 19, 2007

(86) PCT No.: PCT/US2007/073880
§ 371 (c)(1),
(2), (4) Date: May 17, 2010

(87) PCT Pub. No.: WO2009/011702
PCT Pub. Date: Jan. 22, 2009

(65) Prior Publication Data
US 2010/0239659 A1 Sep. 23, 2010

(51) Int. Cl.
| | | |
|---|---|---|
| *A61K 9/14* | (2006.01) |
| *A23J 3/16* | (2006.01) |
| *C08G 63/00* | (2006.01) |
| *C08G 67/00* | (2006.01) |
| *C08G 69/00* | (2006.01) |
| *C08G 75/00* | (2006.01) |
| *A61K 47/48* | (2006.01) |
| *A61K 31/4375* | (2006.01) |

(52) U.S. Cl.
CPC ........ *A61K 31/4375* (2013.01); *A61K 47/488* (2013.01); *A61K 47/48107* (2013.01); *A61K 47/48238* (2013.01); *A61K 47/48692* (2013.01)

(58) Field of Classification Search
None
See application file for complete search history.

(56) References Cited

U.S. PATENT DOCUMENTS

| | | | | |
|---|---|---|---|---|
| 5,942,243 | A | * | 8/1999 | Shah .............................. 424/434 |
| 6,521,736 | B2 | * | 2/2003 | Watterson et al. ........... 528/272 |
| 2006/0269479 | A1 | | 11/2006 | Colton et al. |

OTHER PUBLICATIONS

Mather et al. Progress in Polymer science 2006 31:487-531.*
Cho et al., "Folate receptor-mediated intracellular delivery of recombinant caspase-3 for inducing apoptosis", J. of Controlled Release 2005, 108:121-131.
PCT International Search Report for PCT/US2007/073880 mailed on Aug. 5, 2008.

* cited by examiner

*Primary Examiner* — Robert A Wax
*Assistant Examiner* — Caralynne Helm
(74) *Attorney, Agent, or Firm* — James P. Demers

(57) ABSTRACT

The invention provides amphiphilic biocompatible copolymers which have a hydrophilic backbone and pendant hydrophobic groups. The polymers form nanoscale molecular aggregates in aqueous environments, which have hydrophobic interiors within which anticancer drugs may be solubilized. The polymers optionally feature attached antibodies, receptor ligands, and other targeting moieties which mediate adherence of the drug-carrying aggregates to targeted cancer cells.

15 Claims, 5 Drawing Sheets

SELF-ASSEMBLING AMPHIPHILIC POLYMERS AS ANTI-CANCER AGENTS

FIELD OF THE INVENTION

The present invention relates to the fields of amphiphilic polymers, and specifically to biocompatible micelle-forming comb-type polymers. The invention also relates to the fields of targeted drug delivery and anticancer agents.

BACKGROUND

Amphiphilic block copolymers comprising a hydrophobic block and a hydrophilic block have been well studied in recent years, because of their capacity for self-assembly into a variety of nanostructures as the surrounding solvent is varied. See Cameron et al., *Can. J. Chem./Rev. Can. Chim.* 77:1311-1326 (1999). In aqueous solutions, the hydrophobic compartment of an amphiphilic polymer has a tendency to self-assemble in order to avoid contact with water and to minimize the free interfacial energy of the system. At the same time, the hydrophilic blocks form a hydrated "corona" in the aqueous environment, and so the aggregates maintain a thermodynamically stable structure. The result is a stable, latex-like colloidal suspension of polymer aggregate particles having hydrophobic cores and hydrophilic coronas.

Comb-type amphiphilic co-polymers differ from block co-polymers in that the backbone is largely hydrophobic or hydrophilic, with polymer chains of opposite polarity pendant from the backbone rather than incorporated into it. Comb-type copolymers have been prepared with hydrophobic backbones and hydrophilic branches (Mayes et al., U.S. Pat. No. 6,399,700), and also with hydrophilic backbones and hydrophobic branches (Watterson et al., U.S. Pat. No. 6,521,736; Uchegbu et al., U.S. Application Publication No. 2006/0148982). The former were used to provide multivalent presentation of ligands for cell surface receptors, while the latter were used to solubilize drugs and deliver them to cells.

Amphiphilic polymer aggregates have been studied as carriers for solubilizing insoluble drugs, targeted drug delivery vehicles, and siRNA or gene delivery systems. They have a more stable structure than conventional low-molecular-weight micelles, due to chain entanglement and/or the crystallinity of the interior hydrophobic region. The polymeric nature of the vehicle renders the aggregates relatively immune to the disintegration that ordinary liposomes suffer when diluted below their critical micelle concentration. The absence of a bilayer membrane enables them to more readily fuse with cell membranes and deliver their payload directly to the cell. The amphiphilic nature of the aggregates also confers detergent-like activity, and appropriately targeted aggregates appear to be capable fusing with and disrupting viral coat proteins.

Due to the excellent biocompatibility of poly(ethylene glycol) (PEG), and the apparent ability of PEG-coated "stealth" particles to evade the reticuloendothelial system, micelles, liposomes, and polymers incorporating PEG have been extensively considered as materials for drug delivery systems. There are many reports of the use of PEG as the hydrophilic component of PEG-lipids (forming liposomes and micelles); see for example Krishnadas et al., *Pharm. Res.* 20:297-302 (2003). Self-assembling amphiphilic block copolymers, which self-assemble into the more robust "polymersomes", have also been investigated as vehicles for drug solubilization and delivery. See for example Jones and Leroux, *Eur. J. Pharm. Biopharm.* 48:101-111 (1999); Photos et al., *J. Controlled Release,* 90:323-334 (2003); Kataoka et al., *Adv. Drug Deliv. Rev.* 47:113-131 (2001); and Torchilin, *J. Controlled Rel.* 73:137-172 (2001).

See also Gref et al., *Int. Symp. Controlled Release Mater.* 20:131 (1993); Kwon et al., *Langmuir,* 9:945 (1993); Kabanov et al., *J. Controlled Release,* 22:141 (1992); Allen et al., *J. Controlled Release,* 63:275 (2000); Inoue et al., *J. Controlled Release,* 51:221 (1998); Yu and Eisenberg, *Macromolecules,* 29:6359 (1996); Discher et al., *Science,* 284: 113 (1999); Kim et al., U.S. Pat. No. 6,322,805; Seo et al., U.S. Pat. Nos. 6,616,941 and 7,217,770; Seo et al., European Patent No. EP 0583955. The use of poly(ethyleneimine) (PEI) in this capacity has also been reported, with a focus on delivery of oligonucleotides (Nam et al., U.S. Pat. No. 6,569,528; Wagner et al., U.S. Patent application publication No. 20040248842). In a similar vein, Luo et al., in *Macromolecules* 35:3456 (2002), describe PEG-conjugated polyamidoamine ("PAMAM") dendrimers suitable for delivery of polynucleotides.

In addition to the need to solubilize, distribute, and deliver drugs, there is a need for targeted drug delivery systems that home in specifically on a target cell type, tissue, tumor, or organ. This is usually accomplished by attachment of antibodies or other ligands with a specific affinity for cell walls at the target site. However, PEG lacks functional groups except at the ends of the polymer chains, and in a block copolymer the majority of the terminal groups are inevitably taken up by bonds to the other block copolymer component. For this reason, attachment of targeting moieties such as antibodies or cell-adhesion molecules to PEG block copolymers is generally limited to the non-PEG block, which unfortunately is not the part of the copolymer that is normally exposed in the corona of the self-assembled aggregate.

The phase separation phenomenon which results in the self-assembly of block copolymers into polymer aggregates is readily reversible, and attempts have been made to increase the stability of the aggregates by cross-linking the hydrophobic core (see European Patent No. EP 0552802). Covalent attachment of the drug to the hydrophobic component of a block copolymer has also been attempted (Park and Yoo, U.S. Pat. No. 6,623,729; European Patent No. EP 0397307).

Dendritic polymers are readily conjugated to targeting moieties, and also have the potential to target specific cells in vivo (Singh et al. (1994) *Clin. Chem.* 40:1845) and block adhesion of viral and bacterial pathogens to biological substrates. Comb-branched and dendrigraft polymers conjugated to multiple sialic acid have been evaluated for their ability to inhibit virus hemagglutination and to block infection of mammalian cells in vitro (Reuter et al. (1999) *Bioconjugate Chem.* 10:271). The most effective virus inhibitors were the comb-branched and dendrigraft macromolecules, which showed up to 50,000-fold increased activity against these viruses.

Recently, the pharmaceutical company Starpharma announced the successful development of a dendrimer-based biocide (VivaGel™) that prevents HIV infection by binding to receptors on the virus's surface (Halford (2005) *Chem. & Eng. News* 83 (24):30). Chen at al. (2000) (*Biomacromolecules.* 1:473) have reported that quaternary ammonium functionalized poly(propyleneimine) dendrimers are very potent biocides.

Killing cancer cells without damaging the patient's nearly-identical healthy cells is a particularly difficult proposition. Even with the most successful chemotherapeutic agents, mechanism-based selective toxicity toward cancer cells is only partially attained. For this reason, cancer therapeutics are a class of agents for which targeted delivery is especially desirable, and a great deal of effort has gone into developing ligands for cancer-specific cell surface markers. (Delgado and Francis, *Drug Targeting: Strategies, Principles and Applications*, Humana Press, 2000)

For example, the cell surface receptor for folic acid is often elevated in cancers of the ovary, kidney, lung, breast, brain, and endometrium, and in myeloid cells of hematopoietic origin. Because the folate receptor is usually cryptic in normal cells, but is displayed on the surface of cancer cells, it has frequently been exploited as a target for receptor-directed cancer therapies (Lu and Low, *J Control Release*. 91:17-29 (2003)). Conjugates of folic acid directly with antineoplastic drugs, antibodies (U.S. Pat. No. 5,547,668), liposomes (Liu and Lee, *Drug Design Reviews Online*, 2:547-552 (2005)), and other nanoparticulate drug delivery constructs (Torchilin, *Adv. Drug Delivery Rev*. 58:1532-1555 (2006)) are among the reported applications. Micelles formed from folate-conjugated amphiphilic block copolymers have been shown to selectively deliver paclitaxel to tumor cells (Park et al., *J. Controlled Release* 109:158-168 (2005)).

Similarly, the epidermal growth factor receptor (ErbB1, EGFR) is overexpressed in a wide spectrum of human tumors of epithelial origin, including breast, head and neck, gastric, colorectal, esophageal, prostate, bladder, renal, pancreatic, and ovarian cancers, and non-small cell lung cancer. These findings have established EGFR as another important target for receptor-mediated delivery systems. EGF itself exhibits strong mitogenic and angiogenic activity, which makes it unsuitable as a targeting moiety, but a variety of non-agonist ligands for EGFR have been developed for this purpose.

Antibodies directed against cell-specific or tumor-specific epitopes have been used successfully as targeted therapies, either alone (to activate the patient's complement system) or to deliver radioisotopes or toxins. For example, tositumomab, a murine $IgG_{2a}$ lambda monoclonal antibody directed against the CD20 B-lymphocyte antigen, may be radioiodinated and used to deliver iodine-131 selectively to lymphoma cells. This has proved successful in the clinic as a treatment for non-Hodgkin's lymphoma, and has been commercialized for this indication under the trade name Bexxar™. Similarly, ibritumomab (Zevalin™), another anti-CD20 monoclonal antibody, has been used to deliver yttrium-90 for immunoradiotherapy of non-Hodgkin's lymphoma.

Other clinically-successful cancer-targeting antibodies include alemtuzumab (anti-CD52, Campath™) for chronic lymphocytic leukemia; bevacizumab (anti-VEGF, Avastin™) for colon cancer and lung cancer; cetuximab (anti-EGFR, Erbitux™) and panitumumab (anti-EGFR, Vectibix™) for colon, head and neck cancer; gemtuzumab (anti-CD33, Mylotarg™) for acute myelogenous leukemia; rituximab (anti-CD20, Rituxan™) and epratuzumab (anti-CD22, Lymphocide™) for non-Hodgkin's lymphoma, and trastuzumab (anti-HER-2, Herceptin™) for breast cancer. Of special relevance is the immunotoxin Mylotarg™, in which an anti-CD33 antibody is conjugated to calicheamicin, a cytotoxic antitumor drug.

There remains a need for a drug delivery system that is stable, biocompatible, amenable to the attachment of a variety of targeting moieties, and efficient at delivering a substantial payload of drug to the desired tumor cell targets. There is also a need for targeted anticancer agents that are similarly stable, efficient, and biocompatible.

SUMMARY OF THE INVENTION

The present invention provides biocompatible comb-type polymer molecules, comprising a hydrophilic backbone having branch-point moieties, and hydrophobic branches attached at these branch-point moieties. The branch point moieties further provide attachment points, in form of reactive functional groups, to which targeting moieties specific for tumor cells may be attached. The invention provides aqueous suspensions of polymer aggregates formed from such polymers, and provides methods for solubilizing antitumor agents by encapsulating such agents into the hydrophobic cores of the polymer aggregates. The method for encapsulating the drugs basically comprises contacting the drug species with a polymer of the invention in an aqueous or mixed-aqueous solvent. The resulting drug payload is maintained in a solubilized state within the hydrophobic core of the macromolecular polymer aggregates formed by the comb polymer when it is suspended in the aqueous environment. In preferred embodiments, the polymer aggregate, with its encapsulated drug payload, is selectively delivered to the targeted cancer cells by the targeting moieties.

The invention also provides methods for killing or inhibiting the growth or reproduction of a cancer cell, or for the treatment of cancer in a mammal, which comprises contacting said cancer cell or administering to said mammal an anticancer drug encapsulated within a comb-type polymer consisting essentially of the following structure:

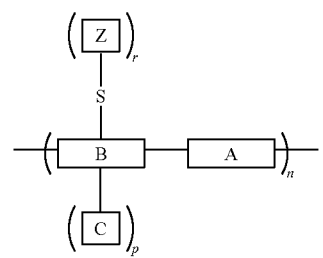

1

The structure comprises a backbone formed of alternating branch-point moieties B and hydrophilic, water-soluble polymer blocks A. Hydrophobic side chains C and, optionally, targeting moieties Z are attached to the branch-point moieties. It will be understood that the polymer chain has terminal groups, typically an H or a polymer block A at the terminal B moiety, and typically an OH at terminal A polymer blocks, but the invention encompasses all convenient chain terminations. Preferably, the side chains C are linear or branched hydrocarbons, optionally substituted with one or more hydrophilic substituents, or $C_6$-$C_{30}$ cyclic or polycyclic hydrocarbons optionally substituted with one or more hydrophilic substituents. Side chains C may also be hydrophobic amino acids, peptides, or polymers. Suitable hydrophilic substituents for the side chains C are hydroxyl, carboxy, and amino groups, as well as amide, sulfonamide, sulfoxide and sulfone groups. Preferred hydrophilic substituents are polar aprotic groups such as tertiary amide, sulfoxide, and sulfone.

The optional targeting moieties Z are ligands or antibodies having specific binding affinity for the surface of a cancer cell. In certain embodiments of the invention, two or more different moieties Z are present on a given branch point or polymer molecule, so that multiple cell-surface receptors and antigens can be targeted as a way of increasing specificity. "Specific binding affinity" means that the ligand or antibody is capable of binding to the surface of the cancer cell in vivo in the presence of the many other cellular surfaces and macromolecules found in the body of the mammal being treated. The affinity may be specific for the cancer cells alone, or for the type of cells which are cancerous in the patient. For example, in a B-cell lymphoma, the ligand may be an antibody to the CD-20 receptor present on all B-cells. The degree of specificity need not be extremely high, but must be sufficient to treat the cancer more effectively than would the solubilized drug payload alone. The moiety represented by "s" is a bond or a spacer moiety, and when s is a spacer each s may carry from 1 to 4 groups Z. The value of n ranges from 1 to about 100; the average value of p ranges from 1 to 2, and in certain embodiments r may be zero. In those embodiments where r is non-zero, the average value of r ranges from 1 to 4.

The branch point moiety B is a multi-valent moiety having bonds to two polymer blocks A, bonds to 1-2 side chains C (on average), and, when r is non-zero, one or more bonds to spacers "s" and/or ligands Z. In particular embodiments, the bonds to B and s and/or Z are established via a plurality of reactive functional groups, which are capable of serving as attachment points. In particularly preferred embodiments, the targeting moieties are covalently attached to the branch-point moieties of the polymers of the invention, and a drug is incorporated into the core of the aggregates, so as to form a targeted drug complex. In other embodiments, if the targeting moiety is an agonist or antagonist of a cell-surface receptor, the targeted polymers or polymer aggregates may exhibit drug-like effects even in the absence of an encapsulated anticancer drug.

The invention further provides methods for the preparation of the comb-type polymers, aggregates, and targeted polymer aggregates and drug complexes described herein. The polymers of the invention self-assemble into polymer aggregates that efficiently solubilize, distribute, and deliver drugs in vivo; are non-toxic, biocompatible, and stable; and are capable of bearing multiple cell-targeting moieties on their exterior surfaces.

DETAILED DESCRIPTION OF THE INVENTION

Figure 1:
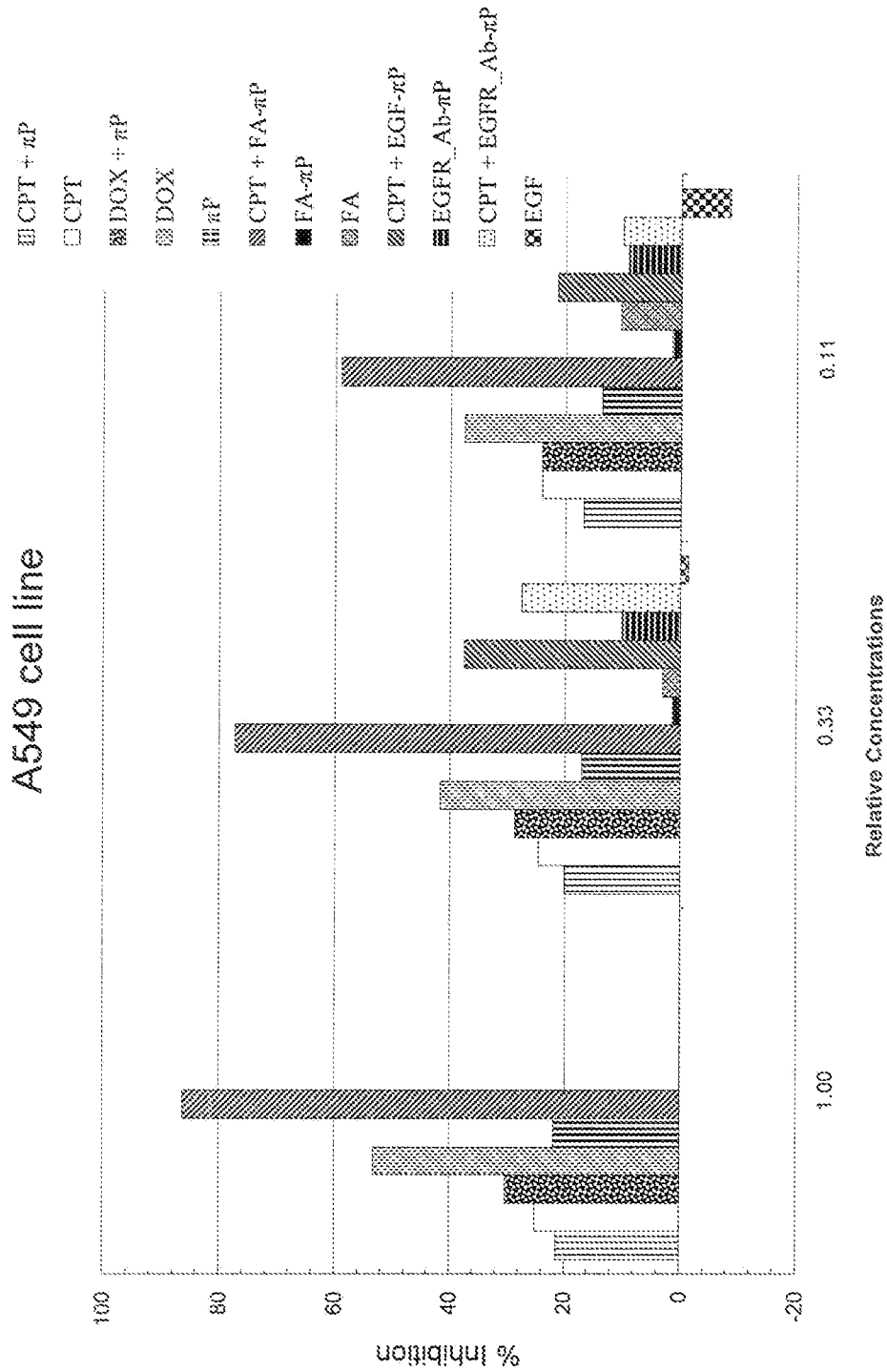
FIG. 1 shows the activity of exemplary compositions of the invention in a cell proliferation assay in a culture of A549 tumor cells.

Examples of the polymers of the invention, referred to herein as "π-polymers", have been described in international application No. PCT/US06/01820, filed Jan. 19, 2006, the specification of which is incorporated herein by reference in its entirety. They have a comb-type architecture, with a backbone formed of alternating branch-point moieties B and hydrophilic, water-soluble polymer blocks A; and having a plurality of hydrophobic side chains C attached to each branch-point moiety, as shown in Formula 1. The side chains C are relatively short, hydrophobic moieties, which may be aliphatic or unsaturated molecules, chains or oligomers. The value of p is ideally an integer, either 2, 3, or 4. In practice the side chains are often introduced via chemical reactions with less-than-perfect efficiency, resulting in an average value of p for the polymer preparation as a whole that is not the intended integer. Non-integer average values can also be obtained by design, as discussed below. Thus, the average value of p in the polymers of the invention is greater than one and may be as high as four ($1<p\leq4$). In preferred embodiments, p ranges from about 2 to 4, and most preferably $1.5<p\leq2$. It should be understood, when an integer value is referred to below, that the integer is idealized and does not refer to the average value actually found in physical samples of the polymers being discussed.

The backbone polymer block A is selected from hydrophilic and/or water-soluble polymer chains, including but not limited to poly(ethylene glycol), poly(propylene glycol), poly(ethylene imine), poly(vinyl alcohol), poly(vinylpyrrolidone), polysaccharides, and the like. Preferably, the polymer units A are poly(ethylene glycol) chains of formula —$(CH_2CH_2O)_m$— where m is between 1 and 10,000, preferably between 3 and 3,000.

In the manufacture of poly(ethylene glycol) of various grades, it is known in the industry to couple a divalent linker moiety (e.g., bisphenol A diglycidyl ether) to two poly(ethylene glycol) chains, effectively doubling the molecular weight of the polymer while retaining a relatively narrow molecular weight range. The resulting "poly(ethylene glycol)" molecules are consequently interrupted at the midpoint of the polymer chain by the non-glycol linker moiety (see, e.g., the poly(ethylene glycol)-bisphenol A diglycidyl ether adduct, CAS registry No. 37225-26-6). Higher oligomers, i.e. those having three PEG chains separated by two bisphenol A diglycidyl ether moieties, are also known, see for example international patent application WO 00/24008. As used herein, therefore, the terms "poly(ethylene glycol)" and "poly(propylene glycol)" encompass poly(ethylene glycol) and poly(propylene glycol) polymer chains that incorporate non-glycol linker units, including but not limited to bisphenol A diglycidyl ether, bisphenol B diglycidyl ether, bisphenol S diglycidyl ether, hydroquinone diglycidyl ether, and the like. For purposes of this specification, any such linker moieties are not counted as "monomer units".

The polymer block A most preferably has an average length of between twenty and fifty monomer units. The polyethylene glycol chains may be end-substituted with functional groups suitable for use as linkers to other moieties, including but not limited to amino, mercapto, acrylate, acrylamide, maleate, maleimide, and the like, at one or both ends. The value of n ranges from 1 to 1000 and is preferably between 3 and 100. The overall molecular weight of the π-polymer may range from 1000 to 100,000 daltons or more; it is preferably above 2,000 daltons, and more preferably above 7,000 daltons.

Hydrophobic moieties C may be the same or different, and may vary from one monomer unit to the next, and may be for example linear hydrocarbons (optionally substituted with one or more hydrophilic substituents), polycyclic hydrocarbons (optionally substituted with one or more hydrophilic substituents), hydrophobic amino acids, peptides and polymers. Suitable hydrophilic substituents include, but are not limited to, hydroxyl, ether, cyano, and amide functional groups. Specifically contemplated are $C_8$ to $C_{20}$ alkyl groups bearing ω-hydroxy, ω-cyano, ω-amido, or ω-alkoxy substituents. In this context, the term "substituent" includes the substitution of a heteroatom, such as O, N, or S, for a carbon atom in the hydrocarbon chain or ring system of the moiety C. Thus, ether and amide linkages, and heterocyclic rings, may be incorporated into the moiety C.

Hydrophobic moieties C are preferably relatively short ($C_8$-$C_{20}$) aliphatic chains, but may also be short oligomers. Suitable oligomers include oligo hydroxy acids such as poly(glycolic acid), poly(DL-lactic acid), poly(L-lactic acid), and copolymers of poly(glycolic acid) and polylactic acid)hydroxy acids, and poly(amino acids), poly(anhydrides), poly(orthoesters), and poly(phosphoesters), polylactones such as poly(epsilon-caprolactone) poly(delta-valerolactone) poly(gamma-butyrolactone) and poly(beta-hydroxybutyrate). C moieties may also be selected from hydrophobic molecules, such as cholesterol, cholic acid, deoxycholic acid, lithocholic acid, and related substances; prostaglandin-like substances; steroidal substances (e.g. dexamethasone); retinoic acids, retinol, and related retinoid substances; hydrophobic peptides; and the like. The molecular weight of each moiety C is greater than 40, preferably between 50 and 1,000, and most preferably between 100 and 500. The logP value (octanol-water) of the molecule C—H is greater than about 1.4, and preferably greater than about 2.0, and more preferably greater than about 2.5. In general, any moiety C is thought to be suitable for use in the present invention if the molecule C—H is substantially insoluble in water. "Substantially insoluble" means that liquid C—H will form a separate phase when mixed with water.

It is a distinguishing feature of the comb polymers of this invention that the side chains C are not regularly and uniformly distributed along the polymer chain, but rather occur in clusters $[C]_p$. These clusters are spaced more or less regularly along the polymer chain, depending on the degree of monodispersity of the polymer units A. Thus, the distance between two side chains C attached to a common branching moiety B is different from the distance between two side chains attached to different branching moieties, which are separated by a polymer block A.

In an embodiment of the invention particularly suitable for targeted delivery, the branch-point moieties B further comprise one or more reactive functional groups X, as shown in Formula 2, which are suitable for the attachment of targeting moieties.

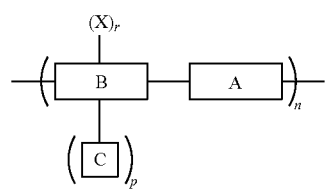

2

In Formula 2, the individual reactive groups X may be the same or may be different from one another, and may optionally be blocked or protected as may be necessary during assembly of the polymer 2. The average value of r will range from 0 (in those embodiments with no X or Z groups) to about 8. Typically, the reactive groups will be selected from functional groups known in the art to be useful for forming covalent linkages between molecular species. In certain embodiments, there may be a single attachment point X. In other embodiments, there may be three or four different types of reactive groups. Suitable reactive groups X include but are not limited to —OH, —NH$_2$, —SH, —CHO, —NHNH$_2$, —COOH, —CONHNH$_2$, haloacyl, acetoacetyl, —CN, —OCN, —SCN, —NCO, —NCS, and the like; reactive double bonds such as vinylic, acrylic, allylic, maleic, cinnamic, and the like, and groups with reactive triple bonds such as acetylenecarboxy and acetylenecarboxamido (suitable for Michael additions, Diels-Alder reactions, and free radical addition reactions).

Exemplary cell-targeting moieties include but are not limited to receptor-specific ligands, antibodies, aptamers or peptides that bind to a specific cell surface receptor, and other targeting moieties, such as peptides possessing an Arginine-Glycine-Aspartic acid (RGD) amino acid sequence or a Tyrosine-Isoleucine-Serine-Arginine-Glycine (YISRG) motif; growth factors including epidermal growth factor (EGF), vascular endothelial growth factor and fibroblast growth factor; cell receptor ligands such as folate, methotrexate, pteroic acid, estradiol, estratriol, testosternone, and other hormones; mannose-6-phosphate, sugars, vitamins, tryptophan, and the like. Receptor agonists and receptor antagonists, whether competitive or allosteric, may be employed.

Aptamers can be selected for binding to a receptor using methods known in the art. Peptides capable of binding to a receptor can be selected using standard methods, such as high-throughput microplate screening, phage display, pin and planar arrays, and the like. Antibodies are preferably monoclonal antibodies directed at cell-specific surface antigens; suitable targeting moieties include not only complete antibodies but also antibody fragments containing the active antigen-binding sequences, such as Fab'2 fragments, Fab' fragments, or short chain peptides (e.g., complementarity-determining region (CDR) peptides) or analogues of the active antigen binding sequences of such antibodies. Suitable antibodies include, but are not limited to, antibodies directed against tumor antigens such as NCA90, NCA95, CEA, CD15, CD20, CD22, CD33, CD52, VGEF, and EGFR. The antibodies are preferably monoclonal, and may optionally be humanized, chimeric, or fully human, and they may be PEGylated or otherwise modified. Polyclonal antibodies may nonetheless be employed with advantage in certain circumstances, due to their multiple antigen-binding capabilities.

Particularly suitable antibodies include, but are not limited to, tositumomab, ibritumomab, alemtuzumab, bevacizumab, cetuximab, gemtuzumab, panitumumab, rituximab, epratuzumab, tositumomab, and trastuzumab, and antibody fragments or peptides comprising the binding domains thereof.

In an alternative embodiment, biotin may be attached to the π-polymer via the functional group X, and used as a non-covalent attachment means for avidin- and streptavidin-coupled proteins, peptides, antibodies, growth hormones, and other targeting moieties.

In certain embodiments of the invention, some fraction of the branch point moieties B are connected to other branch point moieties elsewhere in the polymer chain, so as to form a crosslinked hydrogel structure. Such crosslinking may be effected by reacting the polymer with multifunctional moieties that contain homofunctional or heterofunctional groups, at least one of which reacts with X or a reactive group on C located on a first branch point moiety, and at least one of which reacts with X or with a reactive functional group present on C at a second branch point moiety in the same polymer molecule. Cross-linking may also be made via a link to terminal functional groups on the polymer chain A. As with the linear comb polymers of the invention, such crosslinked polymers may optionally carry targeting moieties.

The branch-point moiety B is typically derived from a multifunctional molecule having a plurality of reactive groups, two of which are suitable for attachment to the hydrophilic polymer unit A, and at least two of which are suitable for attachment of the hydrophobic moieties C. Moiety B may optionally have one or more additional reactive groups X as described above.

Particularly preferred branch-point moieties are the conjugates of dithiothreitol (DTT), dithioerythritol (DTE), or 2,3-diaminobutane-1,4-dithiol with two molecules of maleic acid. The combination of this branch-point moiety with polyethylene glycol as the moiety A generates the polymer backbone of Formulas 3 and 3a

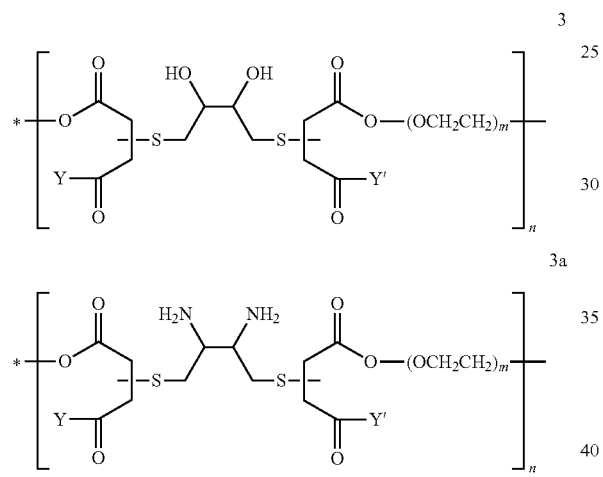

wherein Y and Y' may be the same or different, and are preferably selected from OH, $NH_2$, $ONH_2$, NHOH, and $NHNH_2$. In a preferred embodiment, the hydroxyl or amino groups of the dithiol are the reactive groups X, serving as attachment points for targeting or drug moieties, while the functional groups Y and Y' serve as attachment points for C moieties. Alternatively, the groups Y and Y' may serve as attachment points for targeting moieties, while the hydroxyl or amino groups are used to attach the C moieties.

Formulas 3 and 3a are intended to convey that each sulfur atom may independently be attached alpha or beta to a PEG ester carbonyl group. The invention encompasses single isomer compositions as well as mixtures of regioisomers at one or both C—S bonds. Furthermore, due to the four asymmetric carbons in Formula 1, the invention encompasses all chiral, meso, and diastereomeric isomers and mixtures thereof.

The Diels-Alder adduct of acetylene dicarboxylic acid and a furan may also serve as a suitable branch point moiety. For example, the polyester 4 derived from PEG and acetylenedicarboxylic acid is known to undergo Diels-Alder reactions with furans (M. Delerba et al., Macromol. Rapid Commun. 18(8):723-728 (1997)).

Scheme 1

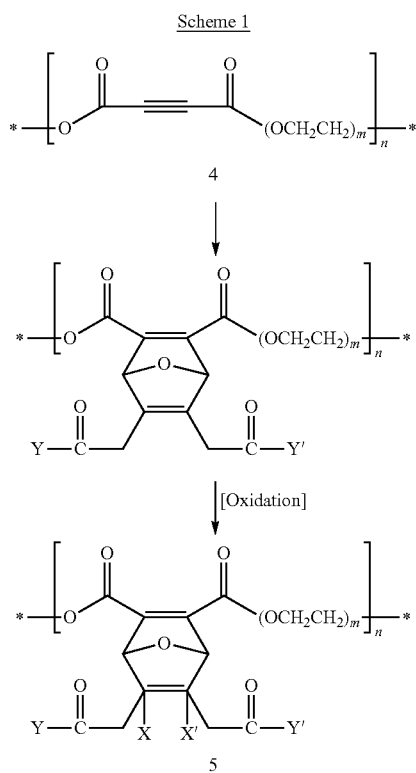

Thus, it may be subjected to a Diels-Alder reaction with a 3,4-disubstituted furan to generate a species such as 5, and polymer 5 can be modified by hydroxylation or epoxidation to provide reactive groups (e.g., X and X' in Scheme 1).

Similarly, reaction of PEG with ethylenediamine tetraacetic acid dianhydride will provide a polyester of formula 6 upon subsequent condensation:

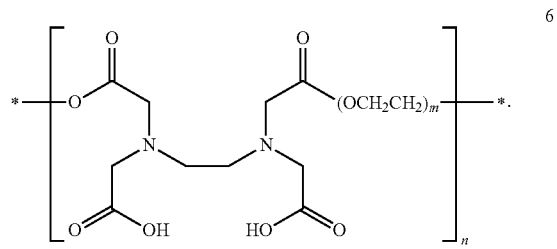

Other suitable branch point moieties may be derived from tartaric acid, acetylenedicarboxylic acid, nitrilotriacetic acid, 3,4,3',4'-diphenyl sulfone tetracarboxylic acid dianhydride, 3,4,3',4'-diphenyl ether tetracarboxylic acid dianhydride, pyromellitic dianhydride, alkanedithiols such as 1,2-ethanedithiol and 1,4-butanedithiol, bis(2-mercaptoethyl) ether, 2-mercaptoethylsulfide, dimercaptopropanol, dimercaptopurine, dimercaptothiadiazole, dimercaptosuccinic acid, benzenedimethanethiols, benzenedithiols, dihalogenated benzenedimethanethiols, dihalogenated 4,4'-thiobisbenzenethiol, and the like.

Where Y and Y' are OH, hydrophobic groups C may be linked to the polymer by amidation or esterification of the carboxylic acid groups. The hydrophobic groups C are preferably relatively small ($C_8$-$C_{20}$) and predominantly hydrocarbon moieties, and may be linear or branched or contain one or more rings. Examples include but are not limited to covalently attached moieties derived from the C—H molecules n-octanol, n-decanol, n-dodecylamine, n-pentadecylamine, cholesterol, deoxycholic acid, cholic acid, retinol, vitamin A and the various cis and trans retinoic acid isomers, the various tocopherols, and arachidonic acid. Although the polymers of the invention are represented, for convenience, as having at most two different hydrophobic side chains, is should be understood that the interior solvent properties of the polymer aggregate may be modified or "tuned" by employing mixtures of two or more hydrophobic compounds, so as to introduce a variety of hydrophobic side chains into a particular polymer. In addition to solvent effects, arising for example from hydrogen bonding and dipole-dipole interactions, physicochemical properties such as liquid crystal phases and phase transition temperatures can be modified. Such effects are well-known, for example from studies of membrane bilayers.

As one specific example, a polymer of formula 2, where X=OH and r=2, was prepared by reacting a polyethylene glycol with maleic anhydride to form the polyester 7, followed by reaction with dithiothreitol to form 8. The acid 7 was then amidated with n-octadecylamine to form the desired comb polymer 9 (Scheme 2). The DTT-derived amide comb polymers represented by formula 9 are referred to herein as "π-Polymer A"; the specific polymer 9 in Scheme 2 is designated "$C_{18}$-π-Polymer A".

Substitution of 2,3-bis(t-butoxycarbonylamino)butane-1,4-dithiol (10a; DuPriest et al., U.S. Pat. No. 4,755,528) for dithiothreitol leads, after deprotection, to the corresponding amino-functionalized π-polymer 9b (Scheme 3).

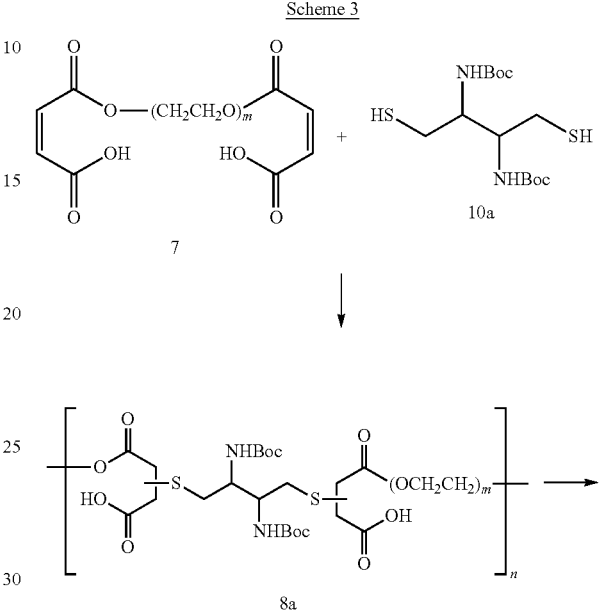

Scheme 3

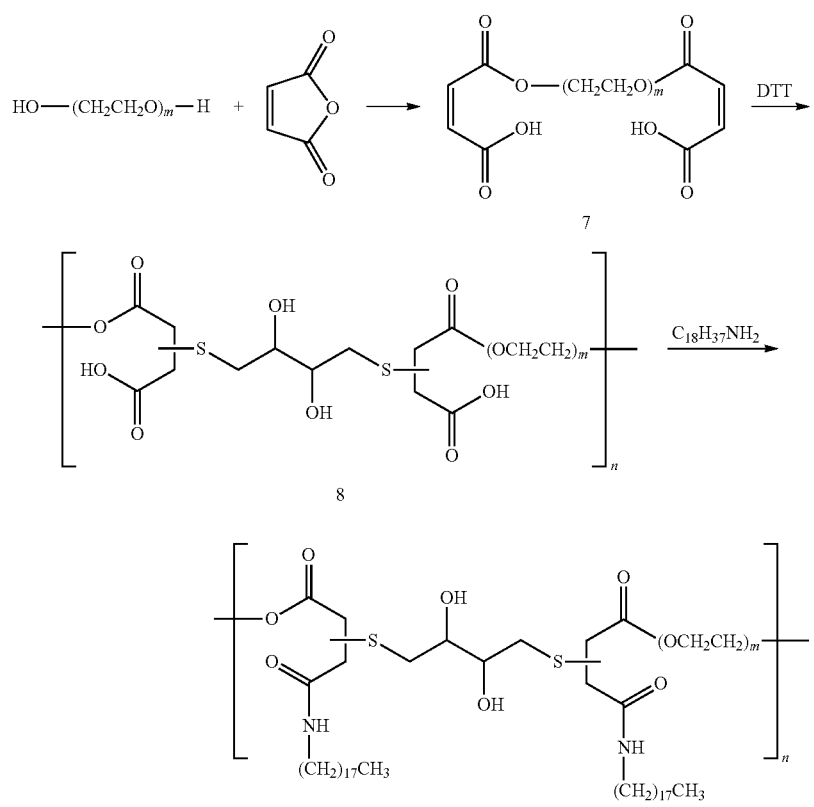

Scheme 2

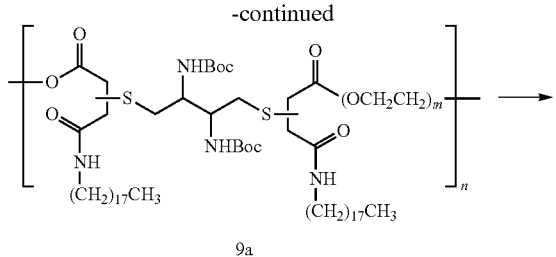

9a

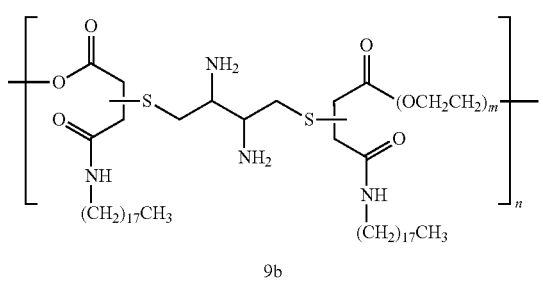

9b

Use of the butanedithiol 10c likewise leads the polymers of general structure 9c, with spacer groups L in place for subsequent attachment of targeting moieties (Scheme 4). The spacer groups L may be any of the spacer groups known in the art for use in attaching ligands or labels to substrate molecules, including but not limited to $C_2$ to $C_{20}$ alkylene and oligo(ethylene glycol) spacers having one to ten —$CH_2CH_2O$— units.

Scheme 4

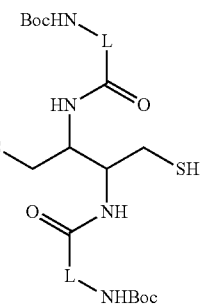

10c

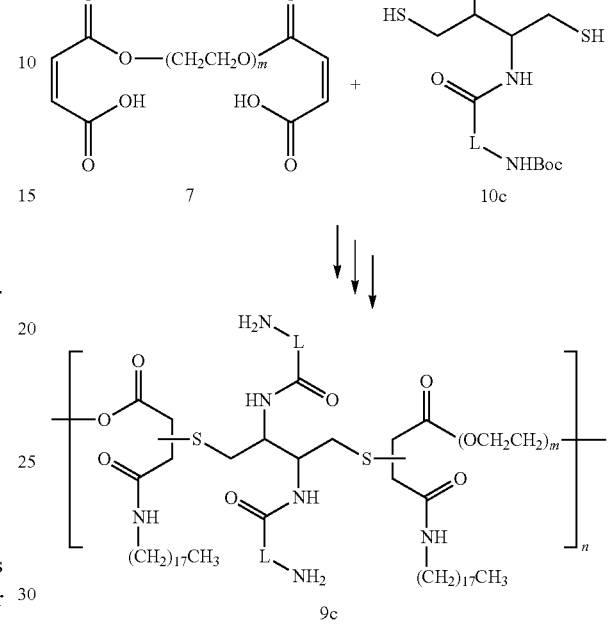

9c

In other embodiments, a PEG polymer with terminal amino groups may be used to prepare examples having amide bonds between the A and B units, as shown in structures 10-14 below. Each of these polyamides may be derived via reaction of the PEG diamine H2N—($CH_2CH_2O$)$_m$$CH_2CH_2$—$NH_2$ with the appropriate cyclic anhydride:

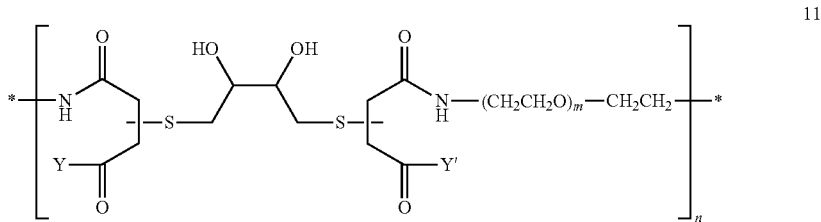

11

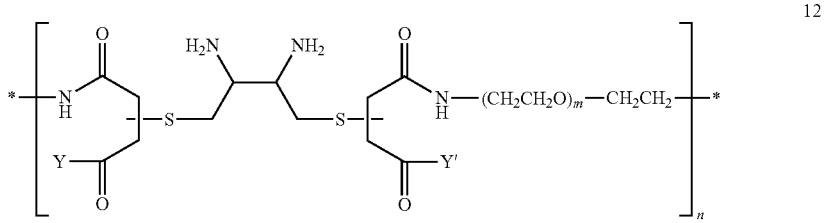

12

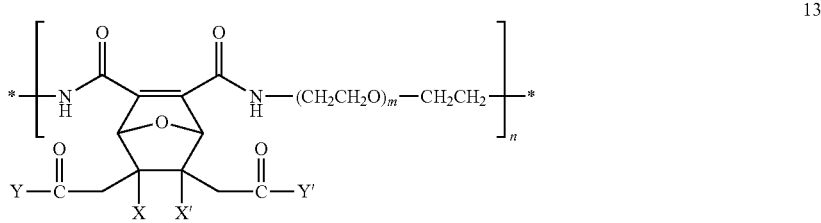

13

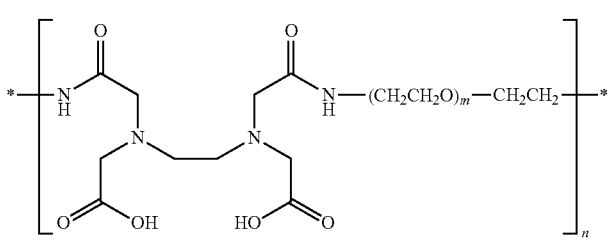

Under mild conditions, the above amido acids are the expected products. Upon heating, imide formation can be expected, leading to polymers with fewer reactive groups but still suitable for attachment of hydrophobic C moieties. Unwanted imide formation can be reduced or avoided by performing reactions at lower temperatures and/or under aqueous conditions. Alternatively, the pendant side chains C can be added to the ends of the polymer A blocks, and the branch point moieties can come into existence at the time of polymerization (Scheme 5).

In addition to simple diamines such as 1,3-diaminopropane, as shown in Scheme 5, diamines having (optionally masked) reactive functional groups X may be employed, leading to polymers 15 suitable for attachment of targeting moieties (Scheme 6). In the formulae below, p may range from 0-4, and each X is independently the same or different from any other group X that may be present. A reactive group X need not be pendant, but may for example be an NH group within the chain of atoms that makes up the diamine, as in the monomer $H_2N-(CH_2)_3-NH-(CH_2)_3-NH_2$.

Scheme 5

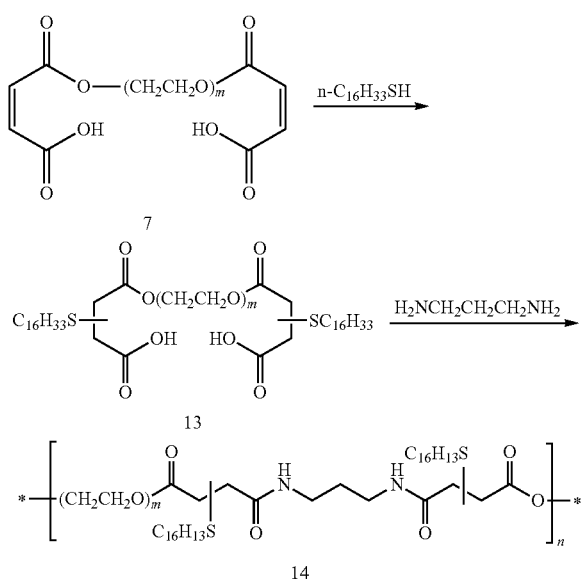

Scheme 6

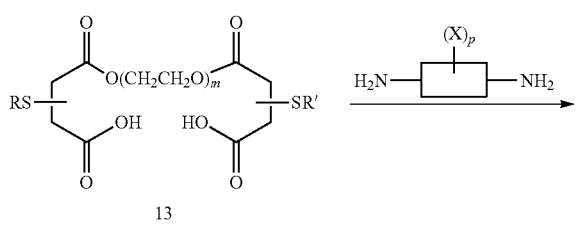

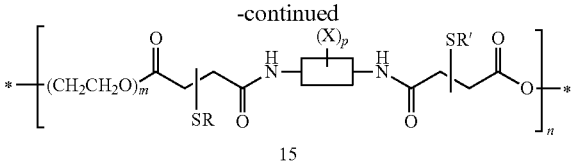

Certain of the π-polymers prepared as above possess reactive groups X suitable for further derivatization, to attach targeting moieties, or to effect crosslinking of the polymer chains via bifunctional or multifunctional cross-linking agents. In particular embodiments, partial derivatization of the reactive groups on the polymer chain is carried out to generate π-polymers having a variety of different reactive groups, which permits attachment of a variety of targeting moieties to a single polymer chain. Thus, addition of a sub-stoichiometric amount of acryloyl chloride (or maleic anhydride) to the π-polymer of Example 1 will provide a polymer with both acryloyl (or maleyl) groups and residual hydroxyl groups. Subsequent Michael addition of a sub-stoichiometric amount of a mercapto-carboxylic acid, for example $HS-(CH_2)_3-COOH$, would provide a polymer with hydroxyl, acryloyl, and carboxyl groups. Addition of cysteine introduces amino and carboxyl groups, in addition to any residual reactive groups left behind by sub-stoichiometric amounts of reagents.

Another approach to polyfunctional π-polymers involves the deliberate omission of a fraction of the hydrophobic chains C. The π-polymer of Example 1, for example, can be prepared with unreacted carboxylic acid groups by the simple expedient of limiting the amount of pendant-forming alkylamine in the amidation step. Yet another approach is amidation with a mixture of amines, a fraction of which contains a reactive group X. Also, under appropriate conditions (excess maleic anhydride in Step A and excess DTT in Step B), a polymer preparation having a desired population of free thiol groups may be generated.

The π-polymer of Example 1 contains, by design, hydroxyl groups derived from the DTT moiety in the backbone, which serve as reactive groups X. Esterification of these groups with acryloyl chloride or methacryloyl chloride in aqueous media in the presence of a carbonate/bicarbonate buffer results in acryloyl substitution on the —OH groups. The acrylated polymer can be readily subjected to radical polymerization (with or without added radical monomer such as an acrylic compound or crosslinker such as a bisacrylic compound) to obtain hydrogels suitable for controlled drug delivery (acting as polymer depots or reservoirs) and for topical applications (such as skin patches or ointments). The acryloyl group can also be subjected to a Michael addition, in particular, with a thiol, such as that of a cysteine residue in a protein, enzyme, peptide, antibody, Fab'2 fragment or Fab' fragment, or other targeting moiety (Scheme 7).

Scheme 7

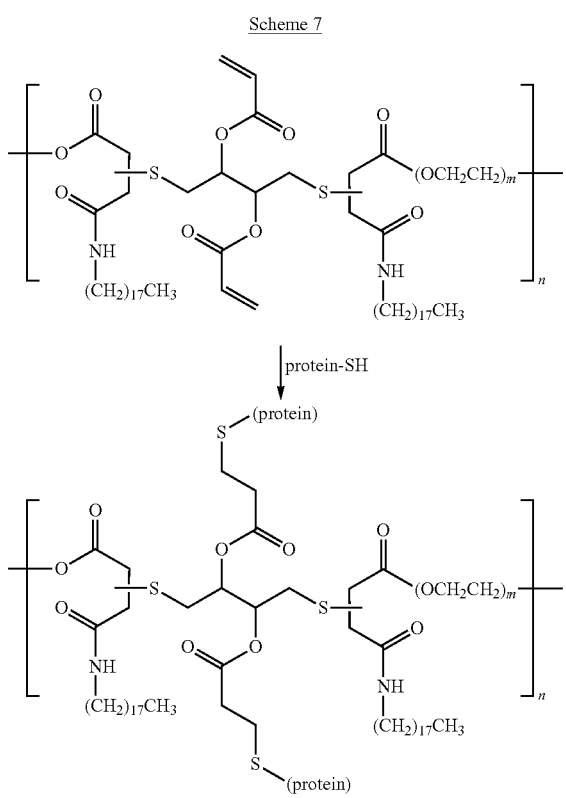

A π-polymer possessing reactive hydroxyl groups, after drying, can also be esterified with maleic anhydride to attach the maleate group, a Michael acceptor, simultaneously generating a free carboxylic group. In the resulting polymer, the maleic double bond is available for a Michael addition, in particular, with a thiol, such as that of a cysteine residue in a protein, enzyme, peptide, antibody, Fab'2 fragment or Fab' fragment, or other targeting moiety. (Scheme 8), and the carboxyl group is available for coupling to amino groups in a targeting moiety, such as the lysine residues in proteins and peptides.

A different moiety may further be attached to the newly introduced (or previously available) carboxylic group via amidation. Thus at least two different targeting moieties can be attached even under saturating reaction conditions (i.e. the moiety to be attached is present in stoichiometric excess).

Scheme 8

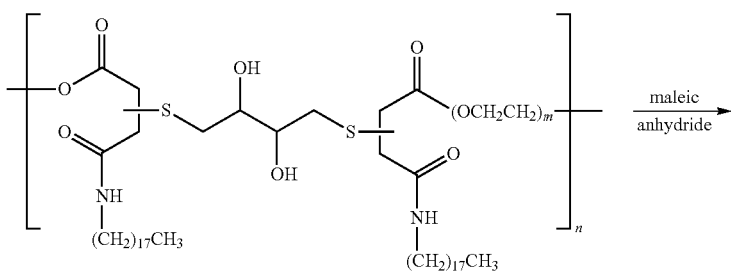

9

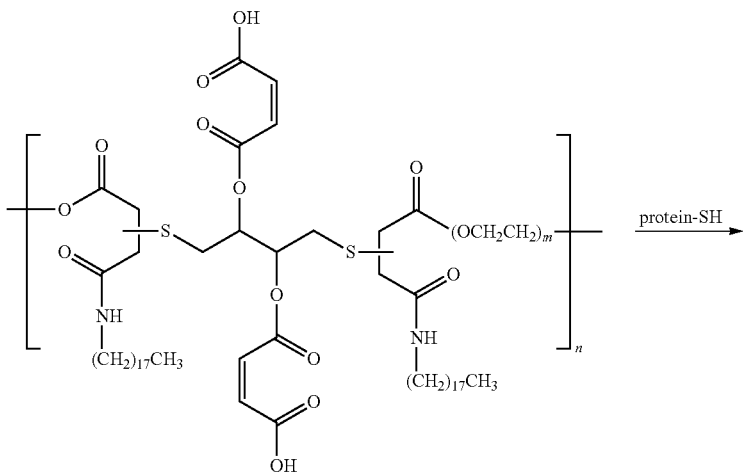

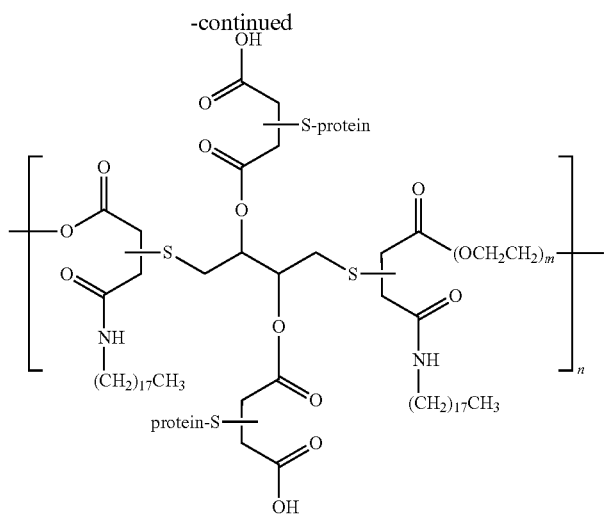

An alternative preparation involves the amidation of PEG dimaleate, followed by reaction with a dithiol, as shown in Scheme 9. Amidation may be carried out via the use of active esters or any of the many known carboxylic acid activation processes, including but not limited to methods employing EDC, DIPC, DCC or the like, with or without further catalysts such as NHS, HOBT, DMAP, pyridine, or TMED. The PEG dimaleamidate is then reacted with DTT or another dithiol to effect a Michael-like addition to the double bond, thereby producing the desired polymer. The advantage of this process is that one may choose, from a potentially very wide selection of preformed PEG dimaleamidates, the precise monomers (and the ratios thereof) that one wishes to incorporate into the polymer.

Scheme 9

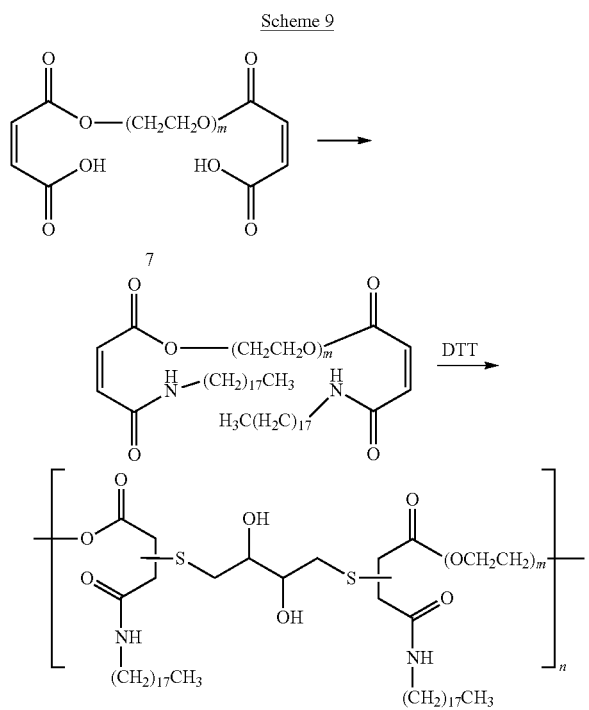

Polymers bearing pendant carboxylate groups may be amidated with amines under typical coupling conditions, and they may also be converted to isocyanate groups via the Curtius rearrangement and then coupled with amines or alcohols to form ureas and carbamates, respectively. Such reactions may be used to introduce the hydrophobic groups C, or to attach targeting moieties.

Free amines can be introduced in the polymer by at least partially reacting one of the reactive groups with a diamine. The diamine must be chosen so that one of the amine groups is either protected or unreactive under the conditions of the reaction. The latter can frequently be accomplished by using ethylenediamine at a pH of about 7.5, since the pKa's of the two amino groups differ considerably. Preferably, this amidation is carried out as a separate step after the introduction of the hydrophobic pendant groups. A peptide or another molecule having a carboxylic group can then be attached by amidation at this free amine.

Thus, even under saturating conditions, as many as three different targeting moieties can be attached to the π-polymer: one via the thiol, one via the amine or hydroxyl, and one via the carboxylic acid group. In addition to targeting moieties, imaging agents may also be incorporated into the polymers of the invention, enabling visualization of the distribution of the polymer in the body. Radiotherapeutic agents such as $^{198}$Au, $^{32}$P, $^{125}$I, $^{131}$I, $^{90}$Y, $^{186}$Re, $^{188}$Re, $^{67}$Cu, $^{211}$At, $^{213}$Bi, $^{224}$Ac, and the like, and cytotoxins such as calicheamicin, bacterial endotoxins, gelonin, abrin, ricin, or the like, may likewise be attached to the polymers.

Hydroxyl and thiol groups can also be converted amines by known methods (e.g. the Mitsunobu reaction), or modified to primary amines by reaction with aziridine or a haloalkyl amine (such as bromoethylamine or chloroethylamine). Amidation with cysteamine will introduce a disulfide, which can be directly reacted with by the cysteine of a peptide or antibody to attach the peptide or antibody; or can be first reduced, e.g., with aminoethanethiol or DTT, for further reaction with a peptide or antibody.

By performing partial reactions, one can introduce additional reactive functional groups to a polymer of the invention, including but not limited to (1) thiol-reactive groups such as acrylic or maleic acid derivatives, (2) carboxylic-acid reactive groups such as amino or hydroxyl, (3) amine-reactive groups such as carboxyl, and (4) disulfide-reactive groups such as mercapto. The number of such added functional groups per polymer molecule may range from 1/r up to several multiples of r, depending on the reagent used and the quantity used.

Alternatively, two or more specific targeting moieties can be attached to improve specificity of binding to a cancer cell surface. Two or more specific moieties can also be used so as to cause an interaction between different targets, for example, one moiety may target the polymer to the cancer cell, and another moiety may facilitate the binding of complement factors and activation of the complement pathway.

Attachment of targeting moieties to the repeating units of the polymers of the invention results in a multivalent display of the moieties on the polymer chain and on the nanoparticle surface. Multivalent display often leads to great increases in affinity for the target. For example, multivalent antibodies can be far more effective in clearance of their targets than the normal divalent antibodies. Carbohydrate-binding proteins and carbohydrates are known to be multivalent in nature, and ineffective if monovalent. Similarly, multivalent peptide and carbohydrate targeting moieties will be far more effective than the monomer alone.

A further benefit of attachment of targeting moieties to the polymer chains of the invention is a substantial increase in molecular weight, which results in reduced renal clearance rates of peptides and other ligands. In addition, the PEG backbone confers benefits similar to those of protein PEGylation, such as the evasion of immune surveillance.

The comb polymers of the invention are useful for encapsulating, in aqueous solvent systems, water-soluble and sparingly water-soluble anticancer drugs. The method of encapsulating a substance in an aqueous solvent comprises contacting the drug with a comb-type polymer of the invention in the presence of water, so as to form a water-soluble complex of the substance and the polymer. Alternatively, the polymer and the substance to be encapsulated may be combined in a two-phase aqueous-organic emulsion, and the organic solvent removed by evaporation. An exemplary process is described in U.S. Pat. No. 6,838,089, incorporated herein by reference. It is believed that in most cases, the polymer self-assembles into micelle-like nanoparticles having the drug dissolved among the hydrophobic C chains that coalesce at the core of the particles, while the A blocks form a hydrophilic corona that sufficiently lowers the interfacial free energy to permit an aqueous suspension of the particles to remain stable.

In some cases, sparingly-soluble drugs may not entirely dissolve in the core, but may exist as solid nanoparticles or nanocrystals surrounded by and suspended in the C chains at the core of the particles. The practice of the invention does not rely on any particular degree of mixing of the C chains with the sparingly-soluble substance. The drug may in some cases dissolve at the molecular level among the C chains, but in other cases it may exhibit any degree of phase separation from the C-chain environment. In some cases, it can be expected that the system will move from one state to the other as a function of external conditions, such as pH, temperature, or shear rate. Shear rate in the bloodstream, for example, can be fairly high, while it is generally low in the lymphatic system. Such environmentally-induced changes in state can be exploited to control drug release from the particle core.

The solvating power of the hydrophobic core of the polymer particles can be modified by modifying the hydrophobic C moieties. Suitable modifications include but are not limited to the introduction of one or more dipolar and/or hydrophilic substituents, such as hydroxyl, ether, amide, sulfoxide, and cyano functional groups, in order to increase the polarity and/or polarizability of the hydrophobic core.

Anticancer drugs that can be encapsulated and delivered by these polymers include but are not limited to doxorubicin, camptothecin, docetaxel, paclitaxel, topotecan, irinotecan, imatinib, sunitinib, sorafenib, axitinib, pazopanib, etoposide, methotrexate, methopterin, dichloromethotrexate, 5-fluorouracil, 6-mercaptopurine, cladribine, cladribine, staurosporine, cytarabine, melphalan, leurosine, actinomycin, daunorubicin, epirubicin, idarubicin, mitomycin D, mitomycin A, caminomycin, aminopterin, tallysomycin, podophyllotoxin, cisplatinum, carboplatin, vinblastine, vincristine, vindesin, retinoic acid, colchicine, dexamethasone, and tamoxifen, and derivatives and analogs of these drugs, as well as photodynamic agents, nucleic acids, nucleic acid analogues, and nucleic acid complexes. Nucleic acid analogues include species such as thiophosphates, phosphoramidates, and peptide nucleic acids. Nucleic acid complexes are ionic complexes of oligonucleic acids or analogues thereof with substantially charge-neutralizing amounts of cationic or polycationic species.

As a result of the ability of the polymers of the invention to encapsulate anticancer drugs, the present invention also provides pharmaceutical compositions, which comprise one or more π-polymers of the invention in combination with a therapeutically effective amount of one or more pharmacologically active anticancer agents, and a pharmaceutically acceptable carrier or excipient. Suitable carriers and excipients include water and saline, and solid additives such as buffers, salts, sugars, polysaccharides such as cellulose and derivatives thereof, and various humectants, glidants, preservatives, binding and dispersing agents known in the art. The polymers of the invention can render effective what would otherwise, in the prior art, have been an ineffective amount of an anticancer agent. For purposes of this disclosure, therefore, a "therapeutically effective amount" is the amount of agent that renders the overall composition effective.

All patents, patent applications, and publications mentioned herein are hereby incorporated by reference in their entirety.

EXAMPLES

1. General Procedures

The invention also provides processes for the preparation of the comb polymers of the invention. Synthesis of these polymers is readily carried out by one skilled in the art of organic synthesis, by following the procedures described below. The key starting material is polyethylene glycol, which is preferably dried and degassed before use. This is conveniently done by stirring molten PEG under vacuum at an elevated temperature, until bubbles stop forming. This may take 8-12 hours, depending on the quality of the PEG. Once dried, the PEG can be stored under argon indefinitely. Commercially available industrial and research grades of PEG may be employed in making the polymers of the invention, for example the polydisperse "PEG 1500" of commerce having a molecular weight distribution of 1430-1570. Such material may incorporate bisphenol A diglycidyl ether, which introduces secondary hydroxyl groups at the center of the PEG chain. In order to ensure that the polymers of the invention have the most reproducible and consistent properties, the PEG is preferably free of bisphenol A, and of low dispersity. Most preferable are PEG polymers that are >95% monodisperse, such as are commercially available from Nektar Therapeutics (formerly Shearwater Polymers), Huntsville Ala., and Polypure AS, Oslo, Norway, An example of a particularly preferred PEG is "PEG-28" from Polypure, which is >95% $HO(CH_2CH_2O)_{28}H$, molecular weight 1252.

All reactions are carried out under an inert atmosphere such as nitrogen or argon, with magnetic or preferably mechanical stirring.

In step A, dry PEG is melted, and maleic anhydride (2 moles per mole of PEG) is added with stirring. The quantity of maleic anhydride should match the number of PEG terminal hydroxyl groups as closely as possible. A shortage of maleic anhydride will result in hydroxyl-terminated polymer chains, whereas an excess of maleic anhydride will consume thiol groups in the next step, leading to premature chain termination and terminal carboxyl groups. The reaction temperature is not critical, and the process can conveniently be carried out at temperatures between 45° C. and 100° C. The preferred temperature of the reaction is between 65° C. and 90° C. If elevated temperatures are employed, the maleic anhydride tends to sublime, and steps should be taken to see to it that the maleic anhydride remains in solution. Minimizing headspace and submerging the reaction vessel in an oil bath are effective methods.

Depending on the temperature selected, the reaction may be completed in 2 hours or less or can be conducted overnight. The reaction may be monitored by TLC on silica gel plates, and is continued until after the disappearance of the maleic anhydride. Visual contrast, UV, and iodine staining can all be used to examine the TLC plates.

In step B, the crude PEG bis-maleate ester produced in step A is combined with dithiothreitol (DTT) and N,N,N', N'-tetramethylethylenediamine (TEMED) (with added water, if necessary for fluidity), and the mixture stirred at 70° C. The reaction is complete within 30 min, as indicated by the rapid increase in viscosity. The molecular weight of the product will be reduced if more or less than the optimal amount of DTT is employed. The molecular weight of the product can also be reduced, if desired, by replacing TEMED with a less effective tertiary amine base such as TEA.

In step C, sufficient water is added to the reaction mixture to reduce viscosity, and 0.1 mol N-hydroxysuccinimide (NHS) and 1.05 mol hexadecylamine per mol carboxylic acid groups in the polymer are added. (This amount of NHS appears to optimally minimize the extent of side-reactions.) An excess of N-(3-dimethylaminopropyl)-N'-ethylcarbodiimide (EDC) (1.4 mol EDC per mol of carboxylic acid groups) is then added in portions, with additional water being added as necessary to maintain stirring. The pH of the reaction mixture is maintained above 7, and preferably between 9- and 11, to optimize the reactivity of the alkylamine. With dodecylamine, this reaction can be conducted at about 40–45° C., whereas with octadecylamine, the temperature is ca. 55° C.-57° C. The reaction is followed by TLC until a constant level of left-over alkylamine is observed, typically after running overnight.

The reaction mixture is acidified to a pH from about 3.0 to about 4.5 and stirred at room temperature for up to about 24 hours to destroy unreacted EDC, then titrated to a pH of 7.0 using 1N NaOH and/or TEMED. The final reaction mixture is centrifuged at about 800×g for 1 to 3 hours, to remove solid contaminants and by-products.

After centrifugation, the supernatant can be chromatographed on a GPC column (Toyopearl™, Sephadex™, Sephacryl™, Biogel™, and the like). The π polymers are amphipathic materials, however, and exhibit affinity for some GPC column packings, which complicates the removal of contaminants. Alternatively, the polymer may be chromatographed on a large-pore hydrophobic interaction column (e.g., TOYOPEARL™ Phenyl 650C, Toshoh Biosciences, Montgomeryville, Pa., U.S.A.), eluting with a gradient of methanol in water. Preferably, the reaction mixture is dialyzed against several changes of acidified and neutral water to remove low-molecular-weight starting materials and reaction by-products.

The reaction mixture may also be extracted with butanone, isopropanol, butanol or other polar organic solvents to remove organic impurities, but substantial amounts of the amphiphilic polymer are lost to the extraction solvent. Preferably, the reaction mixture is subjected to ultrafiltration using suitable membranes to fractionate the product into molecular weight grades, such as 5 kDa to 10 kDa; 10 kDa to 30 kDa, 30 kDa to 50 kDa, etc. depending upon the cutoff of the filtration membrane employed. An aqueous solution of the polymer may be subjected to dead-end filtration so as to produce a sterile or virus-free solution, depending upon the choice of filtration membrane or media.

2. Synthesis of π-polymers

Example 1

PEG-Di(Alkylamidosuccinyl)Dithioether Medium Molecular Weight Polymer (C16-π-Polymer A)

Polyethylene glycol (PEG-1500, Sigma Chemical Co.) was dried under vacuum at 80° C. until bubbles stopped forming. (8-12 hours, depending on the quality of the PEG.) The dried PEG can be stored desiccated under argon indefinitely.

The dried PEG was melted under argon on an oil bath, and maleic anhydride (2 moles per mole of PEG, corrected for purity) was added gradually with stirring. The mixture was stirred under argon at 90° C. Because maleic anhydride tends to sublime, the head space was minimized and the entire reaction vessel was kept at the reaction temperature. Any condensed maleic anhydride on the vessel walls was scraped back into the reaction mixture. The progress of the reaction was monitored by TLC on silica gel plates, using ethanol and hexane as solvents separately, with UV visualization and iodine staining. The reaction was continued for one hour past the disappearance of the maleic anhydride.

The crude PEG dimaleate was diluted with two volumes of water. A solution of dithiothreitol (DTT, 1.01 equivalents per equivalent of PEG) and N,N,N',N'-tetramethyl-ethylene-diamine (TEMED, 1.02 equivalents) in water (2 volumes water per volume of TEMED) was then added to the reaction mixture with stirring. The reaction was stirred at 70° C. under argon for 2.5 hrs, left at room temperature overnight, and then stirred again at 70° C. for 2 hours. The reaction was monitored by TLC and was judged complete upon complete disappearance of the DTT.

Water was added to the above reaction mixture to reduce the viscosity, until the mixture could be stirred (at ca. 25% solids), the mixture was stirred at 65° C. under argon, and N-hydroxysuccinimide (0.1 mol per mol carboxylic acid groups in the PEG-dimaleate-DTT polymer) was added, followed by hexadecylamine (1.05 mol per mol carboxylic acid groups in the polymer) and N-(3-dimethylaminopropyl)-N'-ethylcarbodiimide (EDC, 0.56 mol per mol carboxylic acid groups in the polymer). The mixture was stirred under argon for 1 hour and a second portion of EDC (0.56 mol per mol carboxylic acid groups in the polymer) was added. After another hour, a third portion of EDC (0.28 mol per mol carboxylic acid groups in the polymer, for a total of 1.4 mol EDC per mol of carboxylic acid) was further added to account for loss of EDC to hydrolysis. Additional water was added as necessary to maintain fluidity, as the added solids made the suspension difficult to stir, and the pH was maintained between 3.5 and 7.5 (preferably between 4.5 and 6.5) by addition of 1N NaOH or 1N HCl as needed. The mixture was stirred at 65° C. under argon overnight, monitored by TLC (silica gel, development with ethanol) until the alkylamine appeared to have reached a steady concentration, and was then stirred for an additional 4 h. (With dodecylamine, this reaction was conducted at about 40-45° C., whereas with octadecylamine, the temperature was preferably 55-57° C.) The reaction mixture was then acidified with 1N HCl to a pH of about 4.0-4.5, stirred for 24 h to destroy unreacted EDC, and adjusted to pH 7.0 by dropwise addition of 1N NaOH.

The mixture was transferred to centrifuge bottles and spun in a benchtop centrifuge at about 800×g for 2 hours to separate residual solids. After centrifugation, the reaction mixture was extracted with isopropanol to remove organic impurities. Ultrafiltration is preferred as an alternative to isopropanol extraction.

By this method, the following amino compounds are conjugated to the polymer:
Example 1a: undecylamine
Example 1b: octadecylamine
Example 1c: 4-nonylbenzylamine
Example 1d: 3-[(4-phenoxy)phenyl]propylamine
Example 1e: PEG-Di(alkylamidosuccinyl)dithioether (C16-π-Polymer A, via Scheme 9 alternate route).

PEG (1.5 kD, degassed and dried as described above) was reacted with excess maleic anhydride (more than 2.2 mole equivalent of per mole of PEG) under molten conditions, as described for example 1, and the reaction products dissolved in water and dialyzed against water using a 1 kD cut off membrane. The retentate was evaporated to near-dryness to provide PEG dimaleate suitable for amidation.

PEG dimaleate, dissolved in minimum volume of water (about 1 part water per 2 parts PEG dimaleate) was heated under argon to 70-80° C. in a reaction bottle. The pH was adjusted to 5.0-5.5 with TEMED. To this solution was added 2 mole equivalents hexadecylamine per mole of PEG dimaleate repeat units at 70-80° C. A solution of N-hydroxysuccinimide (2 mole equivalents per mole PEG dimaleate) in a minimum volume of water was then added, followed by an aqueous solution of EDC.HCl (3 mole equivalents per mole of PEG dimaleate) in a slow stream. The mixture was stirred at 70-80° C. until TLC (silica gel, EtOH for development) showed completion of the reaction (hexadecylamine spot unchanging or absent). The reaction mixture was cooled and excess carbodiimide was destroyed by addition of acetic acid until the pH held steady between 2.5 and 3.0. The product was purified by dialysis, first against aqueous EtOH and then against water, or alternatively by precipitation with isopropanol.

The PEG diamide thus formed was dissolved in water, the pH of the reaction mixture was adjusted to between 6.5 and 9 with TEMED, and the temperature raised to 60-70° C. A solution of DTT (1.2 molar equivalent per mole PEG diamide) was added, and the reaction mixture stirred overnight. Excess thiol was quenched with a stoichiometric equivalent of chloroacetamide and TEMED, to give a negative Ellman's test. The product was then purified by dialysis against water, and the retentate was concentrated by evaporation.

Example 2

PEG-Di(alkylamidosuccinyl)dithioether High Molecular Weight Polymer

The procedure outlined in Example 1 was followed, except that 0.55 mol DTT and 0.55 mol TEMED per mol maleic anhydride were used. Vigorous stirring was necessary as the viscosity built up rapidly. It appeared that most of the reaction was complete within 5-10 minutes, followed by slow completion over the next 4 hours as the temperature was raised from 55° C. to 80° C.

Example 3

PEG-Di(Alkylamidosuccinyl)Dithioether Polymer

The procedure outlined in Example 1 was followed, except that 1.5 mol dodecylamine per mol of carboxylic acid groups in the polymer was employed. N-hydroxysuccinimide (NHS, 1.0 mol per mol of carboxylic acid groups) and 1,1'-Carbonyldiimidazole (CDI, 3.0 mol per mol of carboxylic acid groups) were added, and the reaction was stirred at 80° C. for 4 hours and worked up as above.

By this method, the following amino compounds are conjugated to the polymer:
Example 3a: undecylamine
Example 3b: tetradecylamine
Example 3c: octadecylamine
Example 3d: dehydroabietylamine
Example 3e: cholesterol 2-aminoethyl ether
Example 3f: 10-phenoxydecylamine
Example 3g: sebacic acid hydrazide
Example 3h: oleic acid hydrazide
Example 3i: dehydroabietic acid hydrazide
Example 3j: cholic acid hydrazide
Example 3k: palmitic acid hydrazide Example 4

PEG-Co-(Alkylamidosuccinate) Polymer

A solution of PEG (6.66 mmol) and triethylamine (2.32 ml, 16.65 mmol) in dry diethyl ether (10 ml) is cooled at 0° C. under argon and treated dropwise with methanesulfonyl chloride (1.03 ml, 13.32 mmol). Stirring is continued for 1 h at 0° C. and then at room temperature for 2 h. The ether is evaporated and dry acetone (15 ml) is added to the residue in order to precipitate the triethylamine hydrochloride, which is filtered from the solution. The filtrate is treated with lithium bromide (2.31 g, 26.64 mmol) and heated to reflux for 20 h. Then the mixture is diluted with hexane and filtered through a short column of silica (3 cm) covered with Celite™ (0.5 cm), and eluted with hexane. The filtrate is dried, filtered and evaporated to leave α,ω-dibromo-PEG as an oil.

α,ω-Dibromo-PEG is reacted with one equivalent of 2,2-dibutyl-4,5-bis(methoxycarbonyl)-1,3,2-dioxastannolane by the method of Godjoian et al., *Tetrahedron Letters*, 37:433-6 (1996). The resulting dimethyltartrate-PEG polyether is saponified with KOH in methanol, and then amidated with dodecylamine or hexadecylamine as in examples 1 and 3 above, or with the amines in examples 3a-3k.

Example 5

PEG Copolymerization with EDTA Dianhydride

Dry PEG is reacted with ethylenediaminetetracetic acid dianhydride by the method described in Example 1, and is then amidated with dodecylamine as in Example 1 or hexadecylamine as in example 3, or with the amines in examples 3a-3k.

In the same manner, the following dianhydrides are co-polymerized with PEG and subsequently amidated:

Example 5a: Naphthalenetetracarboxylicdianhydride
Example 5b: Perylenetetracarboxylicdianhydride
Example 5c: Benzophenonetetracarboxylicdianhydride
Example 5d: 4,4'-(Hexafluoroisopropylidene)diphthalic anhydride
Example 5e: Butane tetracarboxylic acid dianhydride
Example 5f: Bicyclo(2,2,2)oct-7-ene-2,3,5,6-tetracarboxylic dianhydride
Example 5g: Diethylenetetramine Pentaacetic Acid Dianhydride
Example 5h: 3,4,3',4'-Diphenylsulfone tetracarboxylic acid dianhydride
Example 5i: 3,4,3',4'-Diphenyl ether tetracarboxylic acid dianhydride
Example 5j: Pyromellitic dianhydride Example 6A PEG-Diamine Co-Polymer with Pendant Thioethers PEG dimaleate, prepared as in Example 1, is reacted with dodecanethiol (two equivalents per equivalent of PEG dimaleate) using the same procedure as used for DTT in Example 1. No dilution is necessary, as no polymerization takes place, and the reaction is conducted in molten PEG-dimaleate. The TEMED catalyst is added and then the thiol is added. The reaction is followed by the disappearance of starting materials, using TLC. Temperatures up to the point where the loss of alkylthiol by vaporization becomes significant can be employed (up to ca. 100° C.). A slight excess of alkylthiol may be employed to fully saturate the maleic groups. The excess alkylthiol is driven off at the end of reaction by sparging with nitrogen or argon, and/or heating under vacuum, until none is detected by odor or by TLC.

By this method, the following thiols may be conjugated to PEG dimaleate:
Example 6Aa: mercaptosuccinic acid di-t-butyl ester
Example 6Ab: tetradecanethiol
Example 6Ac: hexadecanethiol
Example 6Ad: 2-mercaptoethanesulfonic acid
Example 6Ae: 3-mercaptopropanesulfonic acid
Example 6Af: 6-mercaptohexanoic acid t-butyl ester
Example 6Ag: 4-mercaptobenzoic acid t-butyl ester
Example 6Ah: mercaptoacetic acid t-butyl ester
Example 6Ai: 4-(t-butoxycarbonylamino)butanethiol
Example 6Aj: 3-(t-butoxycarbonylamino)benzyl mercaptan
Example 6Ak: 4-decylbenzyl mercaptan Thiols having reactive functional groups are suitable for attachment of C chains, and/or the reactive functional groups may serve as attachment points (X) for targeting moieties.

Example 6B

PEG-Diamine Co-Polymer with Pendant Thioethers

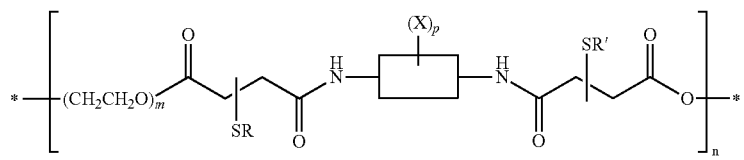

The thiol adduct obtained in Example 6A is amidated with 1,4-diaminobutane (one equivalent of diamine per two COOH groups), using the same procedure used for dodecylamine in Example 1, with dilution with water is as necessary to maintain the fluidity of the reaction mixture. Additional aliquots of EDC are added as necessary to ensure complete polymerization. By this method, the thiol adducts of Example 6A and 6Aa through 6Ak are converted to a PEG-diaminobutane polyamide.

By this method, the following diamines may be converted to a PEG polyamide (BOC=t-butoxycarbonyl):
Example 6Ba: 2-(O-BOC)-1,3-diamino-2-propanol
Example 6Bb: N',N"-di(BOC) hexaethylene tetraamine
Example 6Bc: N',N"-di(BOC) spermine
Example 6Bd: N'-BOC spermidine
Example 6Be: N',N",N'"-tri(BOC) pentaethylene hexamine
Example 6Bf: agmatine
Example 6Bg: lysine t-butyl ester
Example 6Bh: 1,6-diaminohexane
Example 6Bi: 1,4-phenylenediamine
Example 6Bj: 1,3-phenylenediamine
Example 6Bk: 1,4-diaminobutane-2,3-diol acetonide Example 7

PEG-Di(alkylsuccinate)dithioether

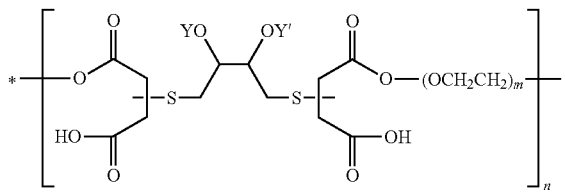

The 2,3-bis-O-hexadecyl ether of DTT (meso-2,3-bis(hexadecyloxy)butane-1,4-dithiol) is prepared by a modification of the procedure of S. Sasaki et al., Chem. Pharm. Bull. 33(10):4247-4266 (1985). This is added to PEG-dimaleate by the method of Example 1.

By this method, the following ether dithiols are coupled to the PEG polymer:
Example 7a: meso-2,3-bis(n-butoxy)butane-1,4-dithiol
Example 7b: meso-2,3-bis(4-nonylphenylmethoxy)butane-1,4-dithiol
Example 7c: meso-2,3-bis(biphenyl-4-methoxy)butane-1,4-dithiol
Example 7d: 4,6-bis(decyloxy)benzene-1,3-dimethanethiol
Example 7e: 4,5-bis(decyloxy)benzene-1,2-dimethanethiol
Example 7f: 3,4-bis(decyloxy)thiophene-2,5-dimethanethiol Example 8A Substituted PEG Succinates The method of Example 1 is followed, except that 2-dodecen-1-yl succinic anhydride is used in place of maleic anhydride. The dodecenyl substituent provides the pendant C chains in the final polymer.

By this method the following substituted succinic anhydrides are esterified with PEG:
Example 8Aa: isobutenylsuccinic anhydride
Example 8Ab: 2-octene-1-yl succinic anhydride
Example 8Ac: octadecenyl succinic anhydride
Example 8Ad: 3-oxabicyclo-hexane-2,4-dione
Example 8Ae: cyclohexanedicarboxylic anhydride
Example 8Af: phthalic anhydride
Example 8Ag: 4-decyl phthalic anhydride
Example 8Ah: hexahydromethylphthalic anhydride
Example 8Ai: tetrahydrophthalic anhydride
Example 8Aj: norbornenedicarboxylic anhydride
Example 8Ak: cantharidin
Example 8Al: bicyclooctenedicarboxylic anhydride
Example 8Am: exo-3,6-epoxy-1,2,3,6-tetrahydrophthalic anhydride
Example 8An: S-acetyl mercaptosuccinic anhydride Example 8B PEG-Di(Alkylamidosuccinyl)Dithioether with Pendant Alkyl Groups By the method of example 1, the substituted PEG succinates obtained as described in Examples 8A and 8Aa through 8An are reacted with DTT.

By this method, the following dithiols are reacted with any of the substituted PEG succinates obtained as described in Examples 8A and 8Aa through 8An:
Example 8Ba: ethane-1,2-dithiol
Example 8Bb: propane-1,3-dithiol
Example 8Bc: butane-1,4-dithiol
Example 8Bd: pentane-1,5-dithiol
Example 8Be: hexane-1,6-dithiol
Example 8Bf: 1,4-benzenedithiol
Example 8Bg: 1,3-benzenedithiol
Example 8Bh: 1,4-benzenedimethanethiol
Example 8Bi: 1,3-benzenedimethanethiol
Example 8Bj: 1,2-benzenedimethanethiol Example 8C PEG-diamine copolymer with pendant alkyl groups By the method of example 6B, the substituted PEG succinate obtained as described in Example 8A is co-polymerized with 1,4-diaminobutane.

By this method, the following diamines are co-polymerized with any of the substituted PEG succinates of Examples 8A and 8Aa through 8An:
Example 8Ca: 2O-BOC 1,3-diamino-2-propanol
Example 8Cb: N',N"-di(BOC) hexaethylene tetraamine
Example 8Cc: N',N"-di(BOC) spermine
Example 8Cd: N'-BOC spermidine
Example 8Ce: N',N",N'"-tri(BOC) pentaethylene hexamine
Example 8Cf: agmatine
Example 8Cg: lysine t-butyl ester
Example 8Ch: 1,6-diaminohexane
Example 8Ci: 1,4-phenylenediamine
Example 8Cj: 1,3-phenylenediamine
Example 8Ck: 1,4-diaminobutane-2,3-diol acetonide Example 9

PEG Trans-Esterification Using Substituted Acids

PEG ditosylate: To 1 mol of PEG (dissolved in DMF or melted as is) was added 2.1 mol of tosyl chloride (5% molar excess) while stirring under argon. To this reaction mixture was added 2.2 mol of tetramethyl ethylene diamine (TEMED). The reaction was then incubated at 45° C. for 2 h. The products were resolved using TLC in ethylacetate, toluene, or ethanol as TLC solvents. The PEG ditosylate may be extracted from the reaction mixture with toluene. Instead of toluenesulfonyl chloride, other sulfonylating agents such as mesyl chloride (see Example 4), triflic anhydride, or tresyl chloride may also be used (see U.S. patent application Ser. No. 10/397,332, Publication No. 20040006051).

Polyesterification of PEG ditosylate: To 1 mol of molten PEG-ditosylate, with stirring under argon, is added 1 mol of S,S'-didecyl-meso-2,3-dimercaptosuccinic acid and 2 mol of TEMED. DMF is added as necessary to maintain fluidity. The reaction mixture is heated to 80° C. and stirred for 24 h or until complete by TLC.

Example 10

PEG-Di(Succinyl)-Di-(O-Acylated)Thioether Medium Molecular Weight Polymer (C16-π-Polymer B)

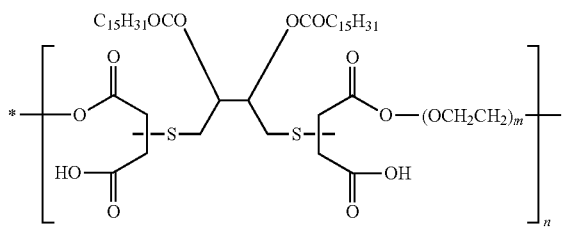

PEG-dimaleate (10.24 g, 6.1 mmols) prepared as in Example 1 was placed in a dry 125 ml flask and heated to 70° C. under argon to melt the PEG-dimaleate. To this molten material, with stirring, was added water (10 mL) and a solution of DTT (0.961 g, 6.168 mmols) and TEMED (0.723 g, 6.166 mmols) in water (3 mL). The solution was stirred at 70° C. for about 4 hr. Removal of water in vacuo gave the solid polymer in about 90% yield.

The dried polymer (5 g, 2.7 mmols) was heated to 70-90° C. under argon to melt it, and TEMED (0.635 g, 5.5 mmols) was added. Palmitoyl chloride (1.689 g, 5.5 mmols) was added with stirring, and the mixture was stirred under argon overnight. (The ratio of polymer to acyl chloride can be varied to obtain degrees of substitution from 0-100% of stoichiometry.) Water was added to the reaction mixture to isolate the "C16-π-Polymer B".

By this method the following acids are esterified with the hydroxyl groups of the di(succinyl)PEG-DTT copolymer:

Example 10a: Oleic acid
Example 10b: Cholesteryl Succinate
Example 10c: Biphenyl-4-carboxylic acid
Example 10d: 4-Octylphenylacetic acid
Example 10e: Hexadec-6-ynoic acid As an alternative to the use of acid halides, the DTT-derived hydroxyl groups of π-polymers may also be activated with 1,3-bis(2,2-dimethyl-1,3-dioxolan-4-ylmethyl)carbodiimide (BDDC) and coupled directly with carboxylic acids; see *Handbook of Reagents for Organic Synthesis, Reagents for Glycoside, Nucleotide, and Peptide synthesis*, Ed. David Crich, Wiley, 2005 p 107-108 and references therein).

Example 11

Carboxyl Substituted Esters of C16-π-Polymer A

Carboxylic acid-substituted polymers are used to attach ligands having reactive amino groups, using standard peptide bond formation methodologies (e.g., via carbodiimide reagents) to link the amino groups to the carboxylic acid functionality of the polymer. These materials are readily obtained by esterification of π-polymer hydroxyl groups with cyclic anhydrides. For example, C16-π-Polymer A dimaleate was prepared by reacting maleic anhydride with C16-π-Polymer A hydroxyl groups as follows:

C16-π-Polymer A (2 g) and maleic anhydride (0.85 g) were ground in a dry mortar and transferred to a 50 mL round bottom flask. The flask was heated at 90° C., under argon, for 2-3 hr with stirring. The solid reaction mixture was then ground and slurried with water, and the mixture was transferred to a dialysis bag (3.5 kDa cut-off). The mixture was dialyzed against water to remove excess maleic acid and low molecular weight by-products, and the retentate was removed from the dialysis bag and dried at 60° C. to constant weight, to give C16-π-Polymer A dimaleate (1.79 g). The ratio of Polymer A to maleic anhydride can be varied to obtain substitutions varying from 0-100% of full stoichiometric esterification.

Example 11a: C16-π-Polymer A diglycolate
C16-π-Polymer A (2 g) and diglycolic acid anhydride (1.0 g) were reacted by the method of Example 11 above, to give C16-π-Polymer A diglycolate. As with maleic anhydride, the ratio of Polymer A to anhydride can be varied to obtain substitutions varying from 0-100% of full stoichiometric esterification.

Example 11b: C16-π-Polymer A bis(aconitate)
C16-π-Polymer A (2 g) and aconitic acid anhydride (1.35 g) were reacted by the method of Example 11 above, to give C16-π-Polymer A bis(aconitate).

In a similar manner, the following anyhydrides are coupled with C16-π-Polymer A. When using anhydrides of low solubility, the pH may be adjusted to between 4.5 and 6.5 prior to dialysis as an aid to purification. A second dialysis against 0.1N HCl provides the acid form of the polymer, if desired.

Example 11c: succinic anhydride
Example 11d: glutaric anhydride
Example 11e: phthalic anhydride The reactive double bond introduced through esterification with maleic or cis-acotinic anyhydride may also be used to add thiol-containing ligands to the polymer, as described in Example 12 below.

Example 12

Cysteine Adduct of C16-π-Polymer A Dimaleate

Powdered C16-π-Polymer A dimaleate (Example 11) (253 mg) was added to water (5 mL) and the mixture was stirred vigorously. Cysteine (24 mg) and TEMED (30.5 ul) were added to the reaction mixture, and the mixture was stirred at room temperature under an argon atmosphere. The progress of the reaction was monitored by TLC (silica gel plates, n-butanol-acetic acid-water, 3:1:1) with detection with ninhydrin. The reaction mixture showed a ninhydrin-positive spot co-migrating with the polymer. Cysteine also gave a ninhydrin-positive spot, whereas the starting polymer did not give any color with ninhydrin.

The method described above was used to introduce additional carboxyl groups for use as attachment points, using thiols having multiple carboxyl substituents. For example, mercaptosuccinic acid was added to the following C16-π-Polymer A diesters:

Example 12a: C16-π-Polymer A dimaleate
Example 12b: C16-π-Polymer A diacrylate
Example 12c: C16-π-Polymer A (bis)aconitate

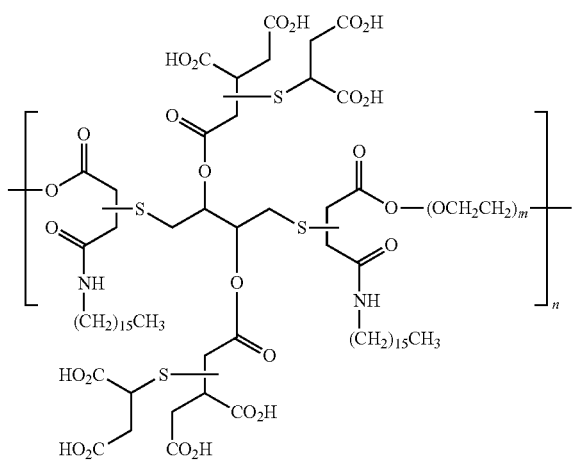

Example 12c

In a similar manner, 3-mercaptoglutaric acid is added to the following C16-π-Polymer A diesters:

Example 12d: C16-π-Polymer A dimaleate
Example 12e: C16-π-Polymer A diacrylate
Example 12f: C16-π-Polymer A (bis)aconitate 3. Attachment of Targeting Moieties to π-Polymers Example 1

Attachment of Folic Acid to C16-π-Polymer a

Folic Acid (2 mmol) was dissolved in anhydrous DMSO and reacted with dicyclohexyl carbodiimide (DCC) at ambient temperature to form the internal anhydride. To this reaction mixture was then added equimolar quantities of cysteamine HCl and TEMED, and the reaction mixture was stirred at ambient temperature for 24 hrs under argon, with monitoring of the reaction by TLC. After the reaction was complete, the reaction mixture was filtered under vacuum to remove reaction byproducts. The filtrate was diluted with methanol to precipitate an orange-yellow product. The precipitate was slurried with methanol and filtered to remove residual dicyclohexylurea urea and DMSO. The folate-cysteamine conjugate (S. Atkinson, *J. Biol. Chem.*, 276(30): 27930-27935) gave a positive test for free sulfhydryl groups with Ellman's reagent, and TLC did not show the presence of cysteamine.

The folate-cysteamine conjugate was then reacted under argon with the dimaleate ester of C16-π-polymer A (Example 11, prepared from PEG having a molecular weight of about 1500). In order to maintain the hydrophilicity of the polymer aggregates, an amount of folate-cysteamine conjugate sufficient to consume only 50% of the available maleate groups was added to the polymer. The pH of the reaction mixture was adjusted to 6.5-7.5 with TEMED, and the mixture was stirred overnight under an argon atmosphere. The reaction mixture was then dialyzed against water with a 3.5 kD cutoff membrane to remove any low molecular weight byproducts and impurities. The retentate was removed and used for the drug encapsulation and cell culture assays described below.

Example 2

Attachment of Epidermal Growth Factor (EGF) to C16-π-Polymer A

Epidermal Growth Factor (Sigma) was thiolated with 2 equivalents of 2-iminothiolane (Sigma) in PBS-EDTA buffer at pH 7.4, and the thiolated EGF was attached to the dimaleate ester of C16-π-polymer A by the method described in example 1. The EGF-conjugated polymer was purified by ultrafiltration and washed with PBS, and the retentate was used to prepare the targeted encapsulated polymer.

Example 3

Attachment of Anti-EGFR Monoclonal Antibody to C16-π-Polymer A

Murine anti-EGFR monoclonal antibody (Sigma) as an ascites fluid was purified by chromatography over AffinityPak™ Immobilized Protein A (Pierce) column per the manufacturer's instructions. The purified antibody was thiolated and conjugated to the dimaleate ester of C16-π-polymer A by the method described in example 1, in PBS buffer at pH 7.4, and purified by ultrafiltration.

4. Encapsulation of Anti-Cancer Compounds

Example 1

Encapsulation of Camptothecin in C16-π-Polymer A

Camptothecin (10 mg, Sigma) was dissolved in DMSO and mixed with a solution of C16-π-Polymer A (100 mg, derived from PEG 1.5 kD) in DMSO. The gel-like mixture was sonicated for about 10-30 minutes, diluted with water, and centrifuged to remove any solids. The clear supernatant tested positive by TLC for the presence of encapsulated camptothecin.

Example 2

Encapsulation of Doxorubicin in C16-π-Polymer A

Doxorubicin HCl (5 mg, Sigma) was dissolved in water and treated with an equivalent of TEMED to convert the hydrochloride to the free amine form. To the resulting free amine form was then added a solution of C16-π-Polymer A (100 mg, derived from PEG 1.5 kD) in DMSO, and the mixture processed and tested as described in Example 1 above.

Example 3

Encapsulation of Camptothecin in Folate-Conjugated C16-π-Polymer A

To the folic acid π-polymer A conjugate synthesized above, dissolved in DMSO, was added a solution of camptothecin in DMSO. A 1:10 ratio by weight of Camptothecin to polymer was used in this preparation. The resulting mixture was processed as in Example 1 above, and gave a positive assay for camptothecin encapsulation.

Example 4

Encapsulation of Camptothecin in EGF-Conjugated C16-π-Polymer A

EGF-conjugated C16-π-Polymer A was used to encapsulate camptothecin, in the same manner as described in Examples 1 and 3 above.

Example 4

Encapsulation of camptothecin in anti-EGFR-conjugated C16-π-Polymer A

C16-π-Polymer A conjugated to murine anti-EGFR antibody was used to encapsulate camptothecin, in the same manner as described in Examples 1 and 3 above.

5. Cell Proliferation Assays

Prior to being evaluated in tumor cell proliferation assays, the examples prepared above were diluted to initial concentrations having the compositions set out below:

CPT+πP

| | |
|---|---|
| Composition: | Camptothecin complexed with π-polymer |
| Repeat unit mw: | 2278 |
| Ligand: | — |
| Ligand mw: | — |
| Encapsulated drug: | camptothecin |
| Drug mw: | 348 |
| Polymer concentration: | .035 mg/ml |
| | 15.4 μM in repeat units |
| Ligand concentration: | — |
| | — |
| Drug concentration: | 3.48 mg/ml |
| | 10.0 μM |

CPT

| | |
|---|---|
| Composition: | Camptothecin (control) |
| Repeat unit mw: | — |
| Ligand: | — |
| Ligand mw: | — |
| Encapsulated drug: | camptothecin |
| Drug mw: | 348 |
| Polymer concentration: | — |
| | — |
| Ligand concentration: | — |
| | — |
| Drug concentration: | 3.48 μg/ml |
| | 10.0 μM |

DOX+πP

| | |
|---|---|
| Composition: | Doxorubicin complexed with π-polymer |
| Repeat unit mw: | 2278 |
| Ligand: | — |
| Ligand mw: | — |
| Encapsulated drug: | doxorubicin |
| Drug mw: | 544 |
| Polymer concentration: | .054 mg/ml |
| | 23.7 μM in repeat units |

-continued

| | |
|---|---|
| Ligand concentration: | — |
| | — |
| Drug concentration: | 5.44 μg/ml |
| | 10.0 μM |

DOX

| | |
|---|---|
| Composition: | Doxorubicin (control) |
| Repeat unit mw: | — |
| Ligand: | — |
| Ligand mw: | — |
| Encapsulated drug: | doxorubicin |
| Drug mw: | 544 |
| Polymer concentration: | — |
| | — |
| Ligand concentration: | — |
| | — |
| Drug concentration: | 5.44 μg/ml |
| | 10.0 μM |

πP

| | |
|---|---|
| Composition: | π-polymer (control) |
| Repeat unit mw: | 2278 |
| Ligand: | — |
| Ligand mw: | — |
| Encapsulated drug: | — |
| Drug mw: | — |
| Polymer concentration: | .035 mg/ml |
| | 15.4 μm in repeat units |
| Ligand concentration: | — |
| | — |
| Drug concentration: | — |
| | — |

CPT+FA-πP

| | |
|---|---|
| Composition: | Camptothecin complexed with folic acid-conjugated π-polymer |
| Repeat unit mw: | 5338 |
| Ligand: | Folic acid |
| Ligand mw: | 441 |
| Encapsulated drug: | camptothecin |
| Drug mw: | 348 |
| Polymer concentration: | .031 mg/ml |
| | 5.81 μM in repeat units |
| Ligand concentration: | 2.56 μg/ml |
| | 5.81 μM |
| Drug concentration: | 3.48 μg/ml |
| | 10.0 μM |

FA-πP

| | |
|---|---|
| Composition: | folic acid-conjugated π-polymer (control) |
| Repeat unit mw: | 5338 |
| Ligand: | Folic acid |
| Ligand mw: | 441 |
| Encapsulated drug: | — |
| Drug mw: | — |
| Polymer concentration: | .031 mg/ml |
| | 5.81 μm in repeat units |
| Ligand concentration: | 2.56 μg/ml |
| | 5.81 μM |
| Drug concentration: | — |

FA

| Composition: | Folic acid (control) |
|---|---|
| Repeat unit mw: | — |
| Ligand: | Folic acid |
| Ligand mw: | 441 |
| Encapsulated drug: | — |
| Drug mw: | — |
| Polymer concentration: | — |
| | — |
| Ligand concentration: | 4.41 µg/ml |
| | 10.0 µM |
| Drug concentration: | — |

CPT+EGF-πP

| Composition: | Camptothecin complexed with EGF-conjugated π-polymer |
|---|---|
| Repeat unit mw: | 5338 |
| Ligand: | EGF |
| Ligand mw: | 6052 |
| Encapsulated drug: | camptothecin |
| Drug mw: | 348 |
| Polymer concentration: | .0868 mg/ml |
| | 16.3 µm in repeat units |
| Ligand concentration: | 910 µg/ml |
| | 150 µM |
| Drug concentration: | 9.05 µg/ml |
| | 26.0 µM |

EGFR_Ab-πP

| Composition: | Anti-EGFR antibody-conjugated π-polymer (control) |
|---|---|
| Repeat unit mw: | 5338 |
| Ligand: | Anti-EGFR antibody |
| Ligand mw: | 150,000 |
| Encapsulated drug: | — |
| Drug mw: | — |
| Polymer concentration: | .106 mg/ml |
| | 19.9 µm in repeat units |
| Ligand concentration: | 3,000 µg/ml |
| | 20.0 µM |
| Drug concentration: | — |
| | — |

CPT+EGFR_Ab-πP

| Composition: | Camptothecin complexed with anti-EGFR antibody-conjugated π-polymer |
|---|---|
| Repeat unit mw: | 5338 |
| Ligand: | Anti-EGFR antibody |
| Ligand mw: | 150,000 |
| Encapsulated drug: | camptothecin |
| Drug mw: | 348 |
| Polymer concentration: | .106 mg/ml |
| | 19.9 µm in repeat units |
| Ligand concentration: | 3,000 µg/ml |
| | 20.0 µM |
| Drug concentration: | 11.0 µg/ml |
| | 31.6 µM |

EGF

| Composition: | EGF peptide (control) |
|---|---|
| Repeat unit mw: | — |
| Ligand: | EGF |
| Ligand mw: | 6052 |
| Encapsulated drug: | — |
| Drug mw: | — |

| Polymer concentration: | — |
|---|---|
| | — |
| Ligand concentration: | 200 µg/ml |
| | 33.0 µM |
| Drug concentration: | — |

The following cell lines were employed, with the specified growth media: A549 (F12 medium), MDAMB231 (Lebovitz's medium), H441, BT474 and SKBR3 (RPMI media). Tumor cells were plated in 96-well plates at 3000 cells/well in complete media with 10% Fetal Bovine Serum and incubated 24 hours at 37° C. Twenty-four hours after plating, test compounds were added in 3-fold serial dilutions, beginning with 10-fold dilutions of the stock solutions described above. Tested dilutions of stock solutions were therefore 10:1, 30:1, and 90:1, and the relative concentrations were 1.00, 0.33, and 0.11 respectively. Six test materials were in short supply; these were diluted directly to 30:1 and not tested at 10:1. Cells were incubated for 72 hours at 37° C. in complete growth media after addition of the test compound. On day 4, using a Promega Cell Titer Glo Luminescent® assay kit, the cells were lysed and 100 microliters of substrate/buffer mixture were added to each well, mixed and incubated at room temperature for 15 minutes. The samples were read on a luminometer to measure the amount of ATP present in the cell lysates from each well, which corresponds to the number of viable cells in that well.

Figure 2:
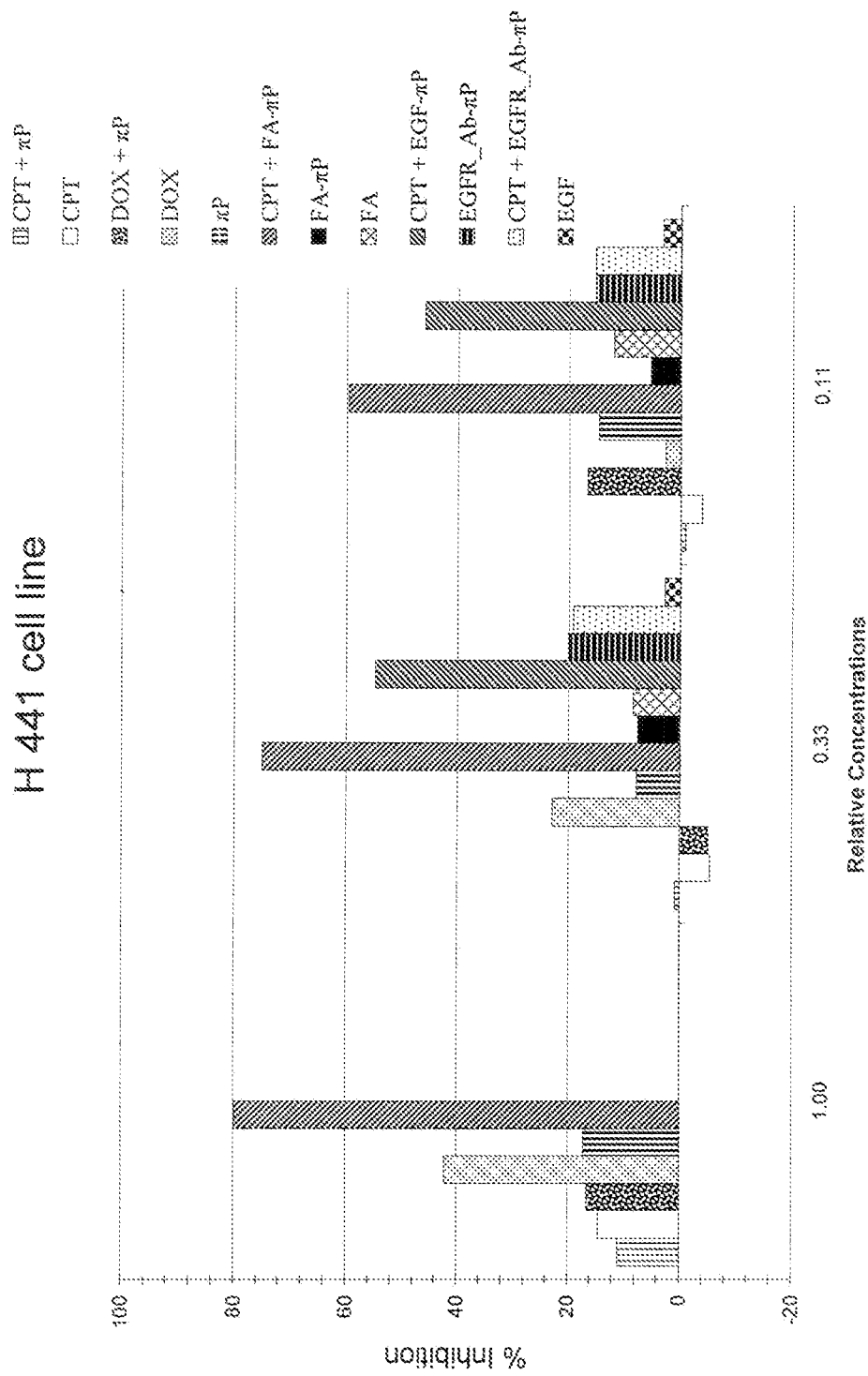
FIG. 2 shows the activity of exemplary compositions of the invention in a cell proliferation assay in a culture of H441 tumor cells.
Figure 3:
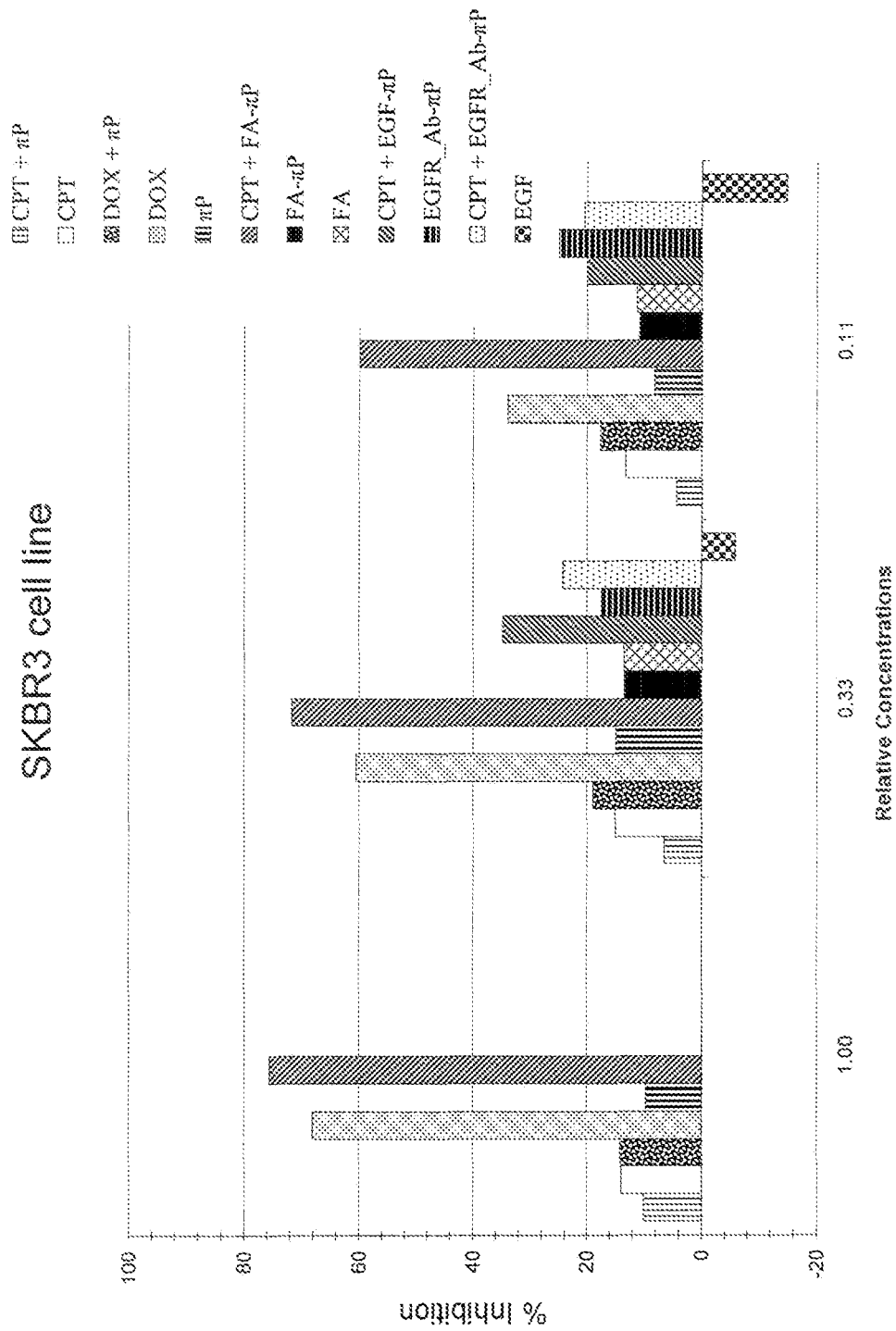
FIG. 3 shows the activity of exemplary compositions of the invention in a cell proliferation assay in a culture of Skbr3 tumor cells.
Figure 4:
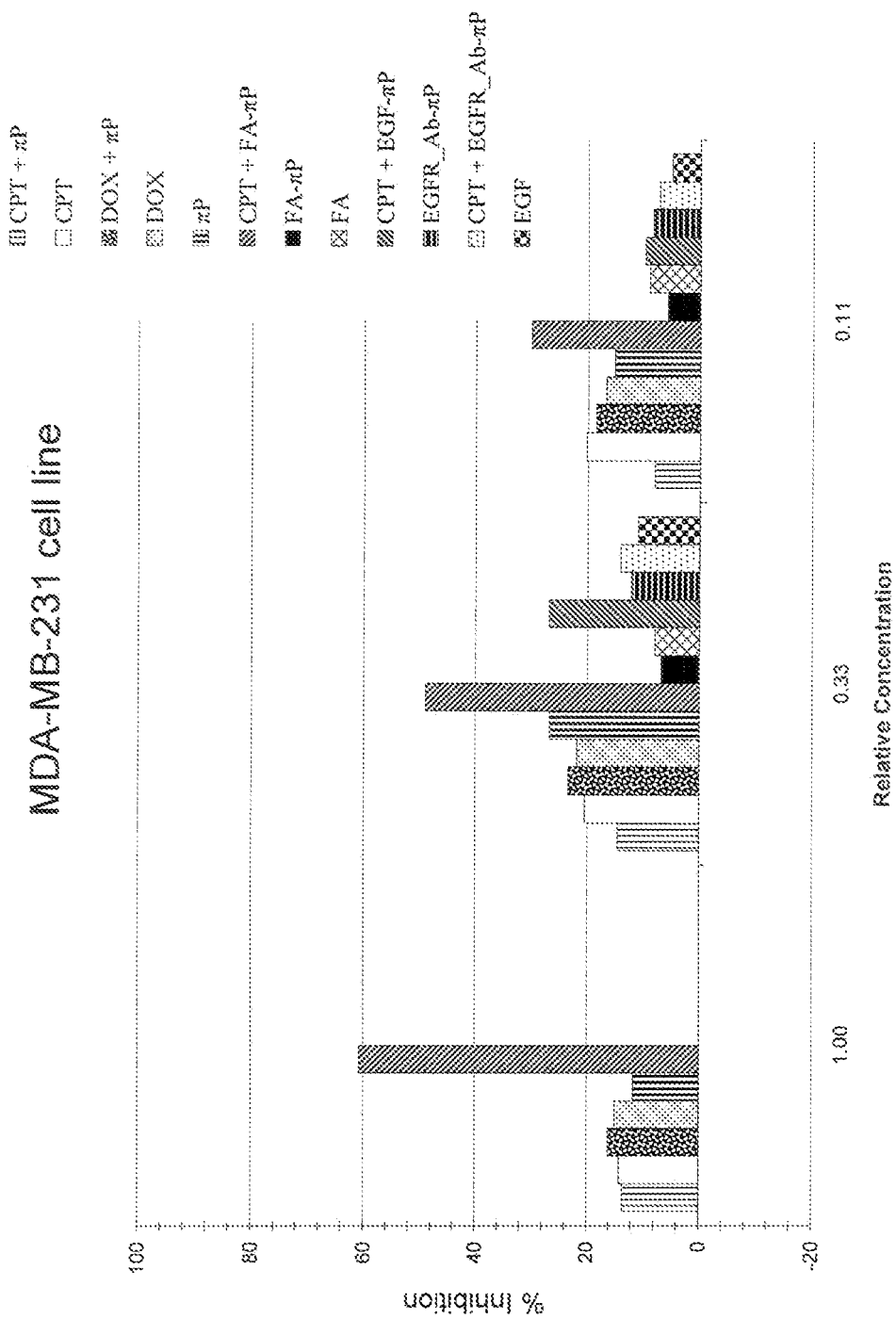
FIG. 4 shows the activity of exemplary compositions of the invention in a cell proliferation assay in a culture of MDA-MB-231 tumor cells.
Figure 5:
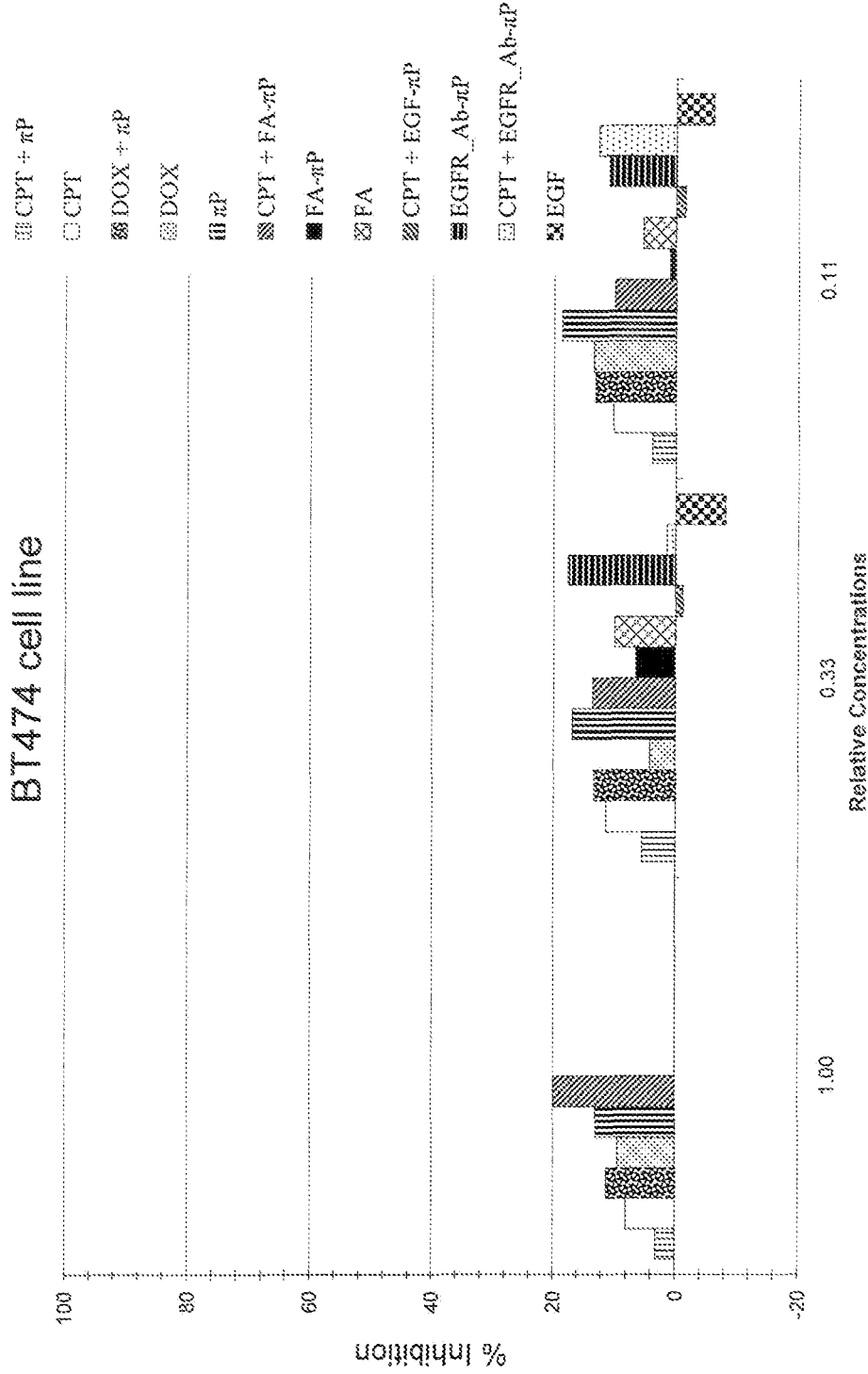
FIG. 5 shows the activity of exemplary compositions of the invention in a cell proliferation assay in a culture of BT474 tumor cells.

Results for each cell line are presented in FIGS. 1-5. A relative concentration of 1.00 represents a 10-fold dilution of the stock solutions described above.

We claim:

1. A method for administering an anticancer drug to cancer cells, which comprises contacting said cancer cells with said anticancer drug encapsulated within a comb polymer, said comb polymer consisting essentially of the following structure:

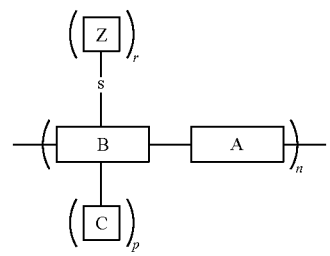

comprising a backbone formed of alternating branch-point moieties B and hydrophilic, water-soluble polymer blocks A; and having a plurality of hydrophobic side chains C attached to each branch point moiety B, and targeting moieties Z attached to the branch-point moieties, wherein:
each branch-point moiety B is a conjugate of dithiothreitol (DTT), dithioerythritol (DTE), or 2,3-diaminobutane-1,4-dithiol with two molecules of maleic acid;
each hydrophobic side chain C has a logP value greater than 1.4, and is independently selected from the group consisting of $C_6$-$C_{30}$ linear or branched hydrocarbons optionally substituted with one or more hydrophilic substituents; $C_6$-$C_{30}$ cyclic or polycyclic hydrocarbons optionally substituted with one or more hydrophilic substituents; and hydrophobic amino acids, peptides and polymers;

each targeting moiety Z is independently a ligand having specific binding affinity for the surface of said cancer cells;

s is a bond or a spacer moiety;

the value of n ranges from 1 to about 100;

the average value of p ranges from greater than one to four; and the average value of r ranges from 0 to 8;

with the proviso that r is non-zero.

2. The method of claim 1, wherein n ranges from 2 to about 100.

3. The method of claim 1, wherein at least one targeting moiety is selected from the group consisting of receptor-specific ligands, antibodies, antibody fragments, and growth factors.

4. The method of claim 2, wherein at least one targeting moiety is selected from the group consisting of receptor-specific ligands, antibodies, antibody fragments, and growth factors.

5. The method of claim 3, wherein said ligand is selected from the group consisting of epidermal growth factor, vascular endothelial growth factor, fibroblast growth factor, folic acid, methotrexate, pteroic acid, estradiol, estratriol, testosterone, mannose-6-phosphate, and antibodies and antibody fragments directed against NCA90, NCA95, CD15, CD20, CD22, CD33, CD52, carcinoembryonic antigen (CEA), vascular endothelial growth factor (VEGF), or epidermal growth factor receptor (EGFR).

6. The method of claim 4, wherein said ligand is selected from the group consisting of epidermal growth factor, vascular endothelial growth factor, fibroblast growth factor, folic acid, methotrexate, pteroic acid, estradiol, estratriol, testosterone, mannose-6-phosphate, and antibodies and antibody fragments directed against NCA90, NCA95, CEA, CD15, CD20, CD22, CD33, CD52, VEGF, or EGFR.

7. The method of claim 1, wherein the anticancer drug is selected from the group consisting of doxorubicin, camptothecin, docetaxel, paclitaxel, topotecan, irinotecan, imatinib, sunitinib, sorafenib, axitinib, pazopanib, etoposide, methotrexate, methopterin, dichloromethotrexate, 5-fluorouracil, 6-mercaptopurine, staurosporine, cytarabine, melphalan, leurosine, actinomycin, daunorubicin, epirubicin, idarubicin, mitomycin D, mitomycin A, caminomycin, aminopterin, tallysomycin, podophyllotoxin, cisplatinum, carboplatinum, vinblastine, vincristine, vindesin, retinoic acid, and tamoxifen.

8. The method of claim 2, wherein the anticancer drug is selected from the group consisting of doxorubicin, camptothecin, docetaxel, paclitaxel, topotecan, irinotecan, imatinib, sunitinib, sorafenib, axitinib, pazopanib, etoposide, methotrexate, methopterin, dichloromethotrexate, 5-fluorouracil, 6-mercaptopurine, staurosporine, cytarabine, melphalan, leurosine, actinomycin, daunorubicin, epirubicin, idarubicin, mitomycin D, mitomycin A, caminomycin, aminopterin, tallysomycin, podophyllotoxin, cisplatinum, carboplatinum, vinblastine, vincristine, vindesin, retinoic acid, and tamoxifen.

9. The method of any of claims 1-8, wherein the polymer block A is selected from the group consisting of poly(ethylene glycol), poly(propylene glycol), and copolymers thereof.

10. The method of claim 9, wherein the polymer block A has an average length of between 4 and 700 monomer units.

11. The method of claim 1, wherein the polymer has the structure

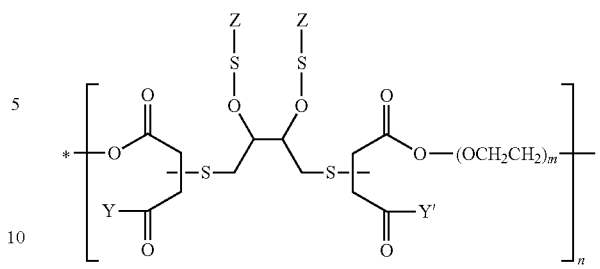

wherein m is 4-700, and each of Y and Y' has a logP value greater than 1.4 and is independently selected from the group consisting of R, OR, COOR, SR, NHR, NRR', ONHR, NHOR, NRNH$_2$, NHNHR, NRNHR', and NHNRR', wherein R and R' are independently selected from the group consisting of $C_6$-$C_{30}$ branched or linear hydrocarbons optionally substituted with one or more hydrophilic substituents, $C_6$-$C_{30}$ cyclic or polycyclic hydrocarbons optionally substituted with one or more hydrophilic substituents, and hydrophobic amino acids, peptides and polymers.

12. The method of claim 1, wherein the polymer has the structure

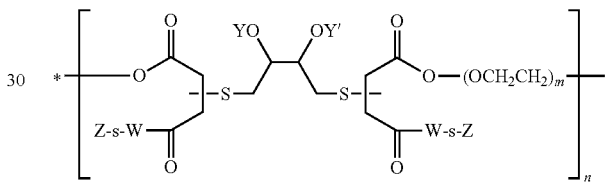

wherein m is 4-700, W is O or NH, and each of Y and Y' has a logP value greater than 1.4 and is independently selected from the group consisting of R, COR, COOR, CONHR, CONRR', CONHOR, CONRNH$_2$, CONHNHR, CONRNHR', and CONHNRR', wherein R and R' are independently selected from the group consisting of $C_6$-$C_{30}$ branched or linear hydrocarbons optionally substituted with one or more hydrophilic substituents, $C_6$-$C_{30}$ cyclic or polycyclic hydrocarbons optionally substituted with one or more hydrophilic substituents, and hydrophobic amino acids, peptides and polymers.

13. The method of claim 1, wherein the polymer has the structure

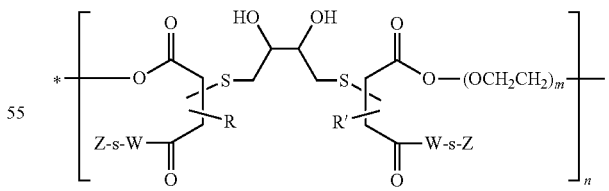

wherein m is 4-700, W is O or NH, and each of R and R' has a logP value greater than 1.4 and is independently selected from the group consisting of $C_6$-$C_{30}$ branched or linear hydrocarbons optionally substituted with one or more hydrophilic substituents, $C_6$-$C_{30}$ cyclic or polycyclic hydrocarbons optionally substituted with one or more hydrophilic substituents, and hydrophobic amino acids, peptides and polymers.

14. A pharmaceutical composition comprising one or more pharmaceutically acceptable carriers or excipients, and an anticancer drug encapsulated within a comb polymer, said comb polymer consisting essentially of the following structure:

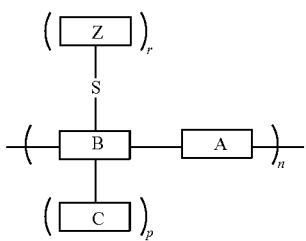

comprising a backbone formed of alternating branch-point moieties B and hydrophilic, water-soluble polymer blocks A; and having a plurality of hydrophobic side chains C attached to each branch point moiety B, and targeting moieties Z attached to the branch-point moieties, wherein:

each branch-point moiety B is a conjugate of dithiothreitol (DTT), dithioerythritol (DTE), or 2,3-diaminobutane-1,4-dithiol with two molecules of maleic acid;

each hydrophobic side chain C has a logP value greater than 1.4, and is independently selected from the group consisting of $C_6$-$C_{30}$ linear or branched hydrocarbons optionally substituted with one or more hydrophilic substituents; $C_6$-$C_{30}$ cyclic or polycyclic hydrocarbons optionally substituted with one or more hydrophilic substituents; and hydrophobic amino acids, peptides and polymers;

each targeting moiety Z is independently a ligand having specific binding affinity for the surface of said cancer cells;

s is a bond or a spacer moiety;

the value of n ranges from 1 to about 100;

the average value of p ranges from greater than one to four; and the average value of r ranges from 0 to 8;

with the proviso that r is non-zero.

15. The pharmaceutical composition of claim 14, wherein n ranges from 2 to about 100.

* * * * *